(12) United States Patent
Hofland et al.

(10) Patent No.: US 9,440,056 B2
(45) Date of Patent: Sep. 13, 2016

(54) DEVICE AND METHOD FOR DISPENSING A DRUG

(71) Applicant: Dermira, Inc., Menlo Park, CA (US)

(72) Inventors: Hans Hofland, Menlo Park, CA (US); Delphine Caroline Imbert, Menlo Park, CA (US); Daniel O'Connell, Broughton (GB); Allen Pearson, Broughton (GB)

(73) Assignee: Dermira, Inc., Menlo Park, CA (US)

( * ) Notice: Subject to any disclaimer, the term of this patent is extended or adjusted under 35 U.S.C. 154(b) by 0 days.

(21) Appl. No.: 14/869,799

(22) Filed: Sep. 29, 2015

(65) Prior Publication Data

US 2016/0089526 A1     Mar. 31, 2016

Related U.S. Application Data

(60) Provisional application No. 62/057,064, filed on Sep. 29, 2014, provisional application No. 62/108,344, filed on Jan. 27, 2015.

(51) Int. Cl.
| | |
|---|---|
| *A61M 35/00* | (2006.01) |
| *B05B 11/00* | (2006.01) |
| *B05C 17/00* | (2006.01) |
| *A61M 39/00* | (2006.01) |
| *A61M 37/00* | (2006.01) |
| *A61M 29/00* | (2006.01) |
| *A61H 33/04* | (2006.01) |
| *A61F 7/00* | (2006.01) |

(52) U.S. Cl.
CPC ......... *A61M 35/003* (2013.01); *B05B 11/0037* (2013.01); *B05B 11/308* (2013.01); *B05B 11/3059* (2013.01); *B05C 17/00* (2013.01); *A61M 2210/04* (2013.01)

(58) Field of Classification Search
CPC .... A61M 35/00; A61M 37/00; A61M 29/00; A61H 33/04; A61F 7/00
See application file for complete search history.

(56) References Cited

U.S. PATENT DOCUMENTS

| | | | |
|---|---|---|---|
| 502,590 | A | 8/1893 | Sill |
| 2,961,679 | A | 11/1960 | Claypool |
| 3,655,952 | A | 4/1972 | Johnson et al. |
| 4,402,427 | A | 9/1983 | Muskovin et al. |
| 4,445,626 | A | 5/1984 | Steffen et al. |
| 4,526,294 | A | 7/1985 | Hirschmann et al. |

(Continued)

FOREIGN PATENT DOCUMENTS

| | | |
|---|---|---|
| GB | 890348 | 2/1962 |
| WO | WO 95/34340 A1 | 12/1995 |

(Continued)

OTHER PUBLICATIONS

International Search Report and Written Opinion for Application No. PCT/US2015/053030, Dec. 2, 2016, 28 pgs.

*Primary Examiner* — Michele Kidwell
*Assistant Examiner* — Ilya Treyger
(74) *Attorney, Agent, or Firm* — Squire Patton Boggs (US) LLP

(57) ABSTRACT

A device for dispensing a topically administered drug has a spreader which is used to actuate a pump to release the drug and then to spread the drug on the skin and. The spreader is coupled to a lock that prevents it from actuating the pump after a number of drug doses have been dispensed. The pump can be actuated to release no more than the selected quantity of drug per day or actuation.

22 Claims, 26 Drawing Sheets

(56) References Cited

U.S. PATENT DOCUMENTS

| | | |
|---|---|---|
| 5,469,989 A | 11/1995 | Graf et al. |
| 6,164,498 A | 12/2000 | Faughey et al. |
| 6,758,620 B1 | 7/2004 | Harrold |
| 7,232,043 B2 | 6/2007 | Wong et al. |
| 7,871,217 B2 | 1/2011 | Kennedy et al. |
| 8,215,861 B2 | 7/2012 | Gueret |
| 8,267,610 B2 | 9/2012 | Goodman |
| 8,425,474 B2 * | 4/2013 | Glassman ............ A61M 31/00 206/528 |
| 9,006,462 B2 | 4/2015 | Statler et al. |
| 9,073,066 B2 | 7/2015 | Banks et al. |
| 2005/0129455 A1 | 6/2005 | Avalle |
| 2006/0163276 A1 | 7/2006 | Wong et al. |
| 2010/0083964 A1 * | 4/2010 | Brown ............ A61M 15/0065 128/203.15 |

FOREIGN PATENT DOCUMENTS

| | | |
|---|---|---|
| WO | WO 2009/086009 A1 | 7/2009 |
| WO | WO 2013/057223 A1 | 4/2013 |

* cited by examiner

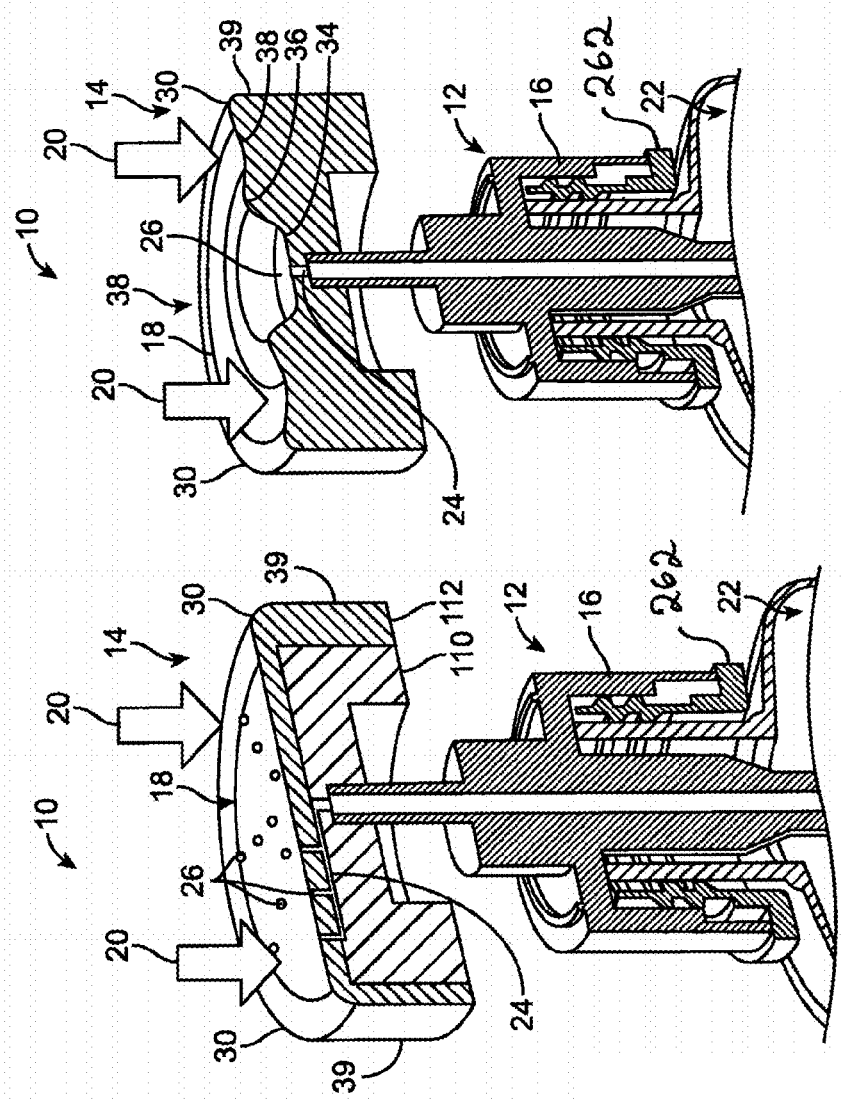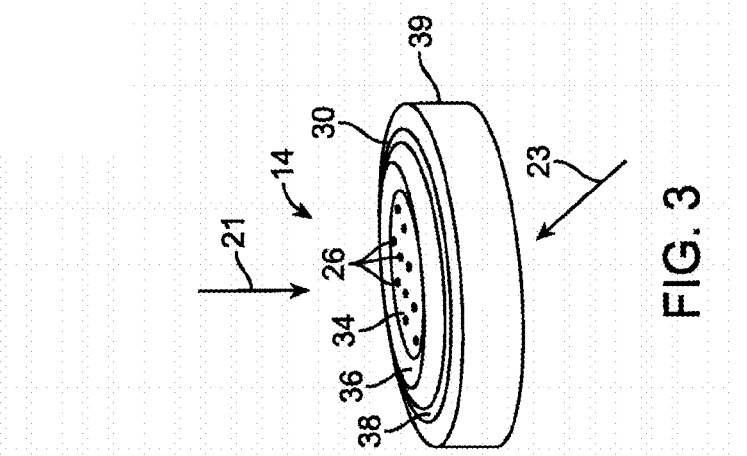

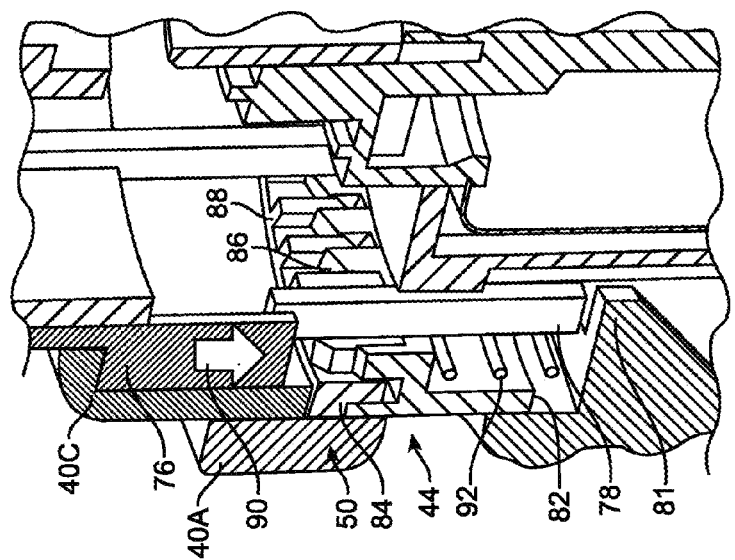
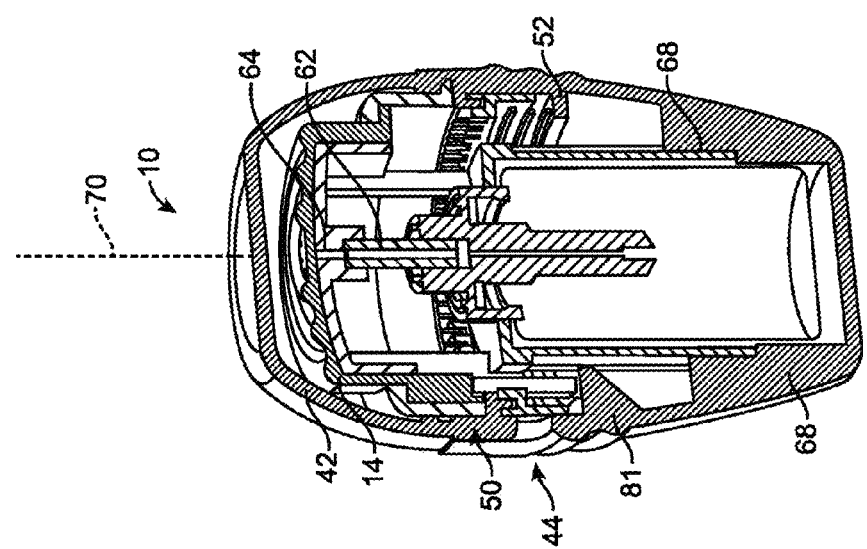
FIG. 6
FIG. 7

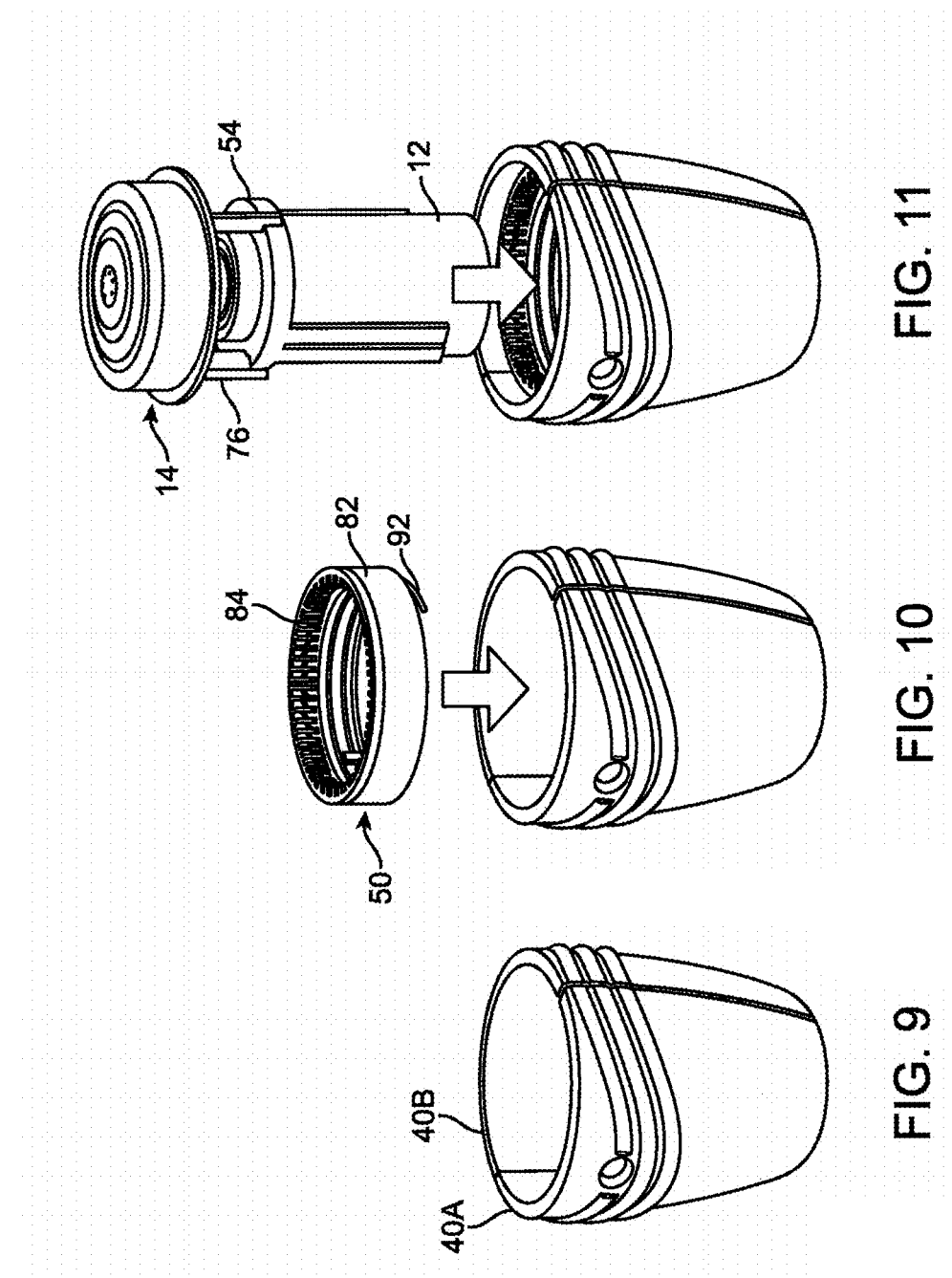

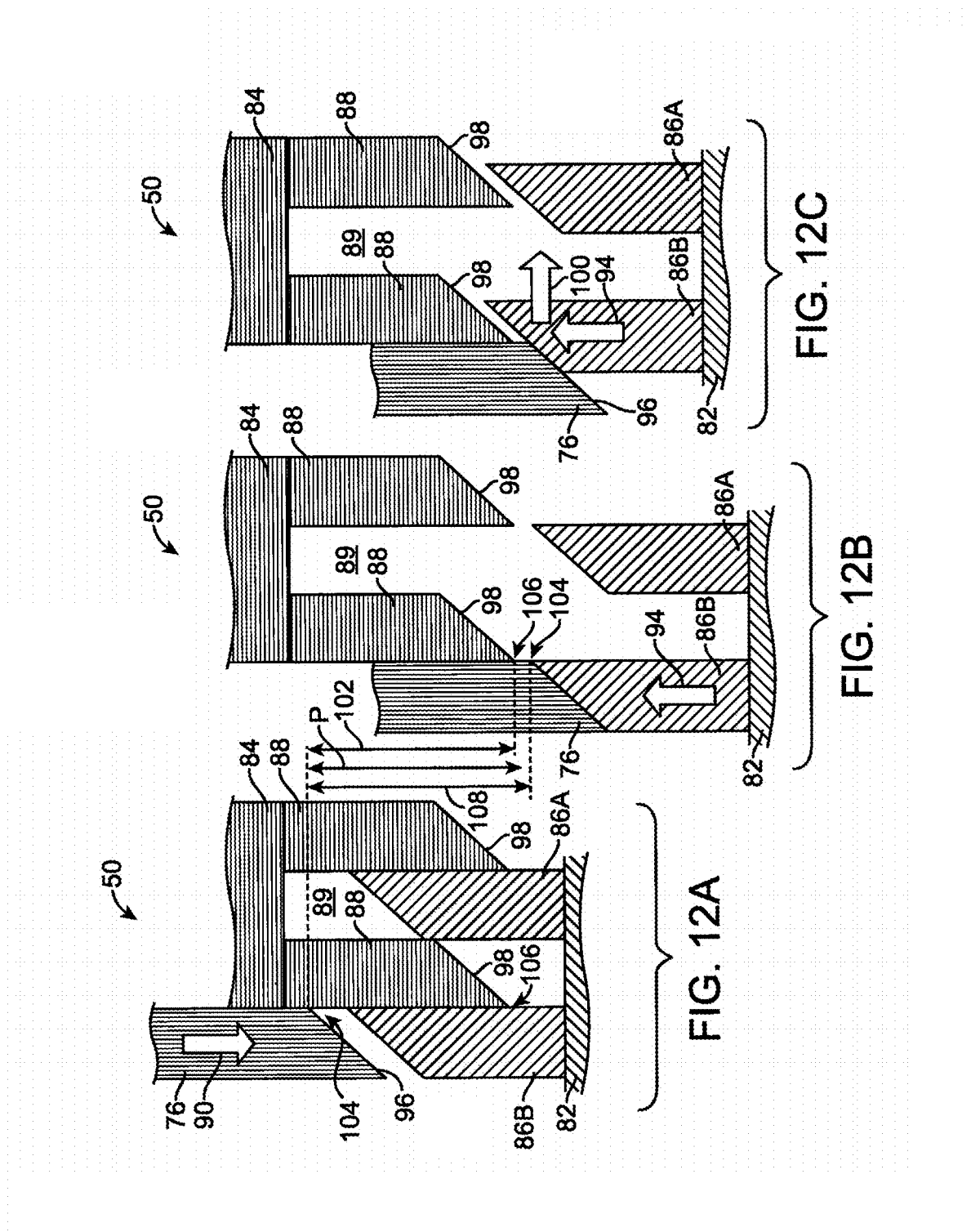

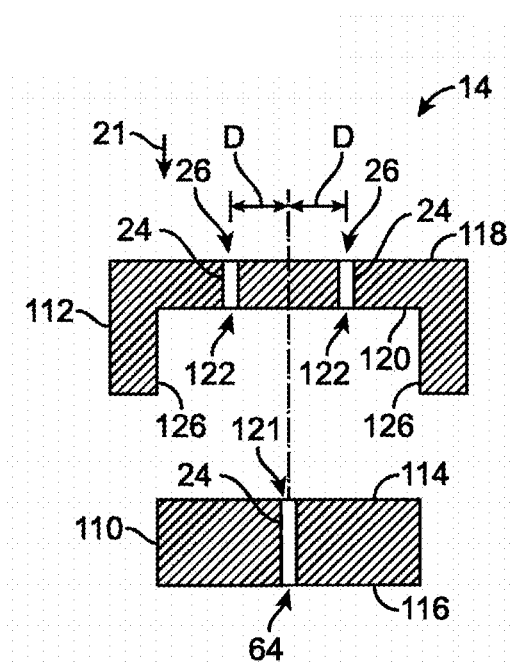
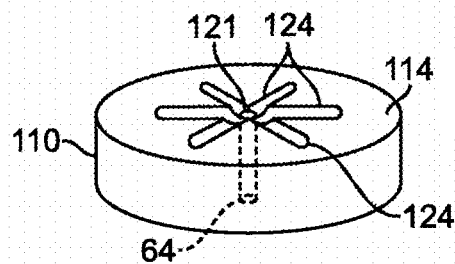
FIG. 13
FIG. 14
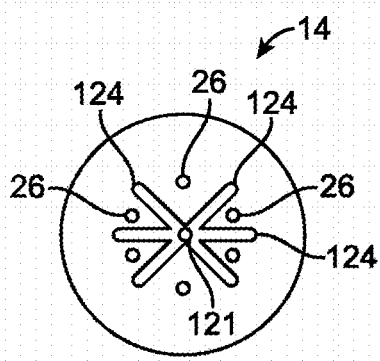
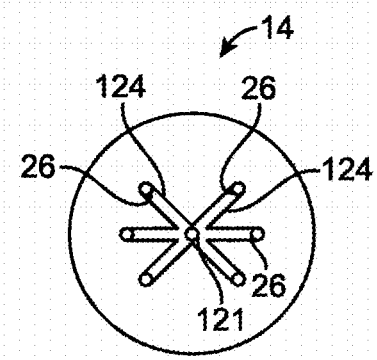
FIG. 15A
FIG. 15B
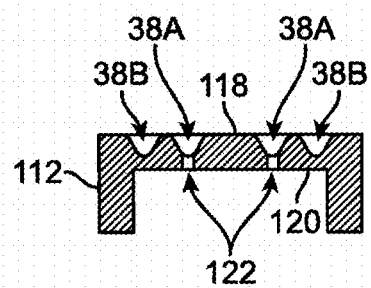
FIG. 16

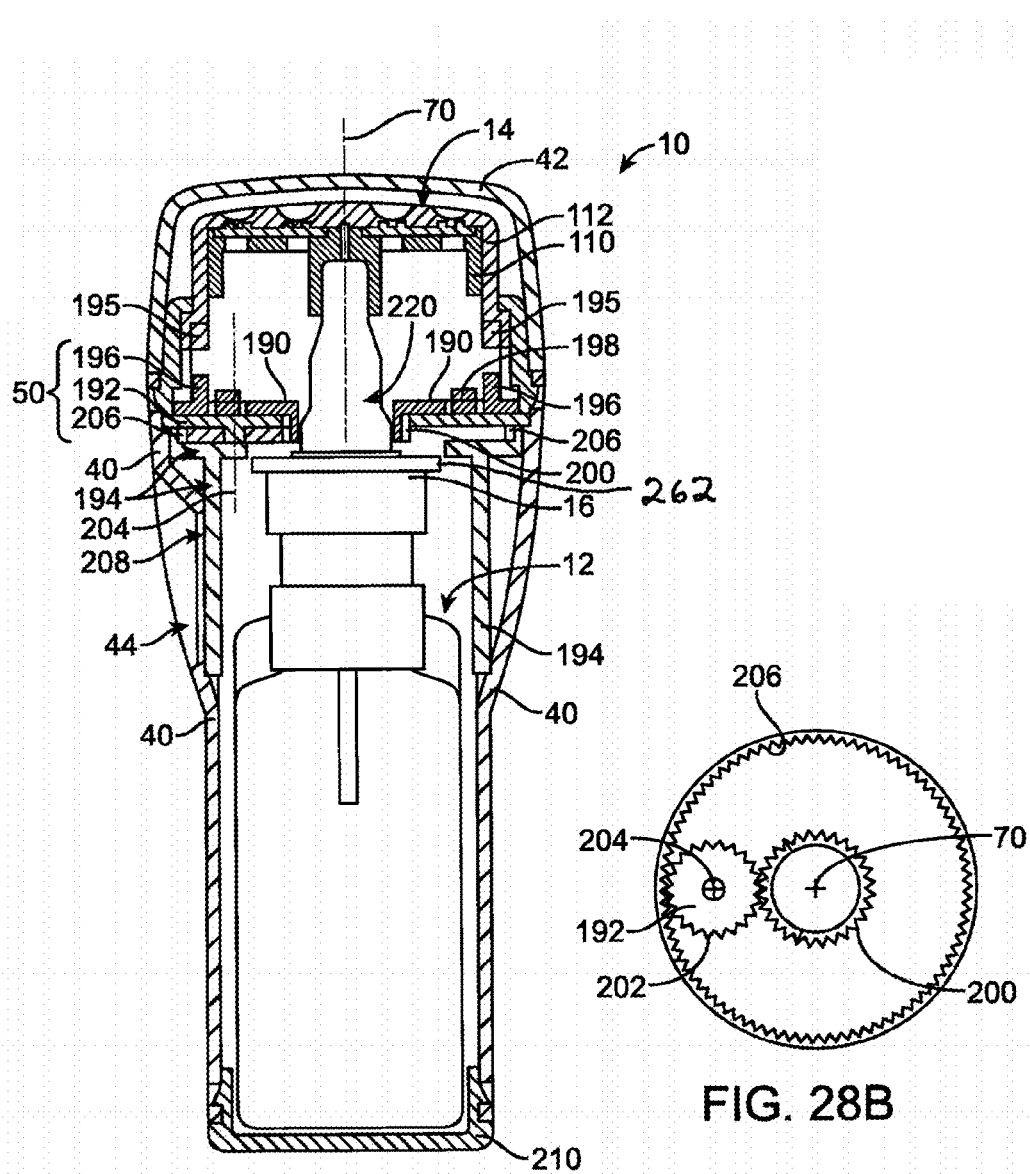
FIG. 28A
FIG. 28B
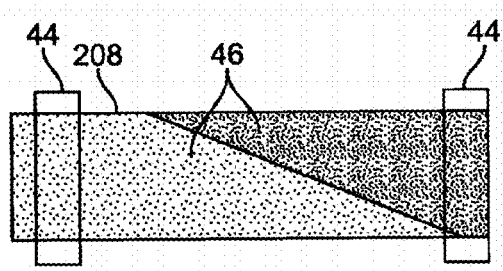
FIG. 28C

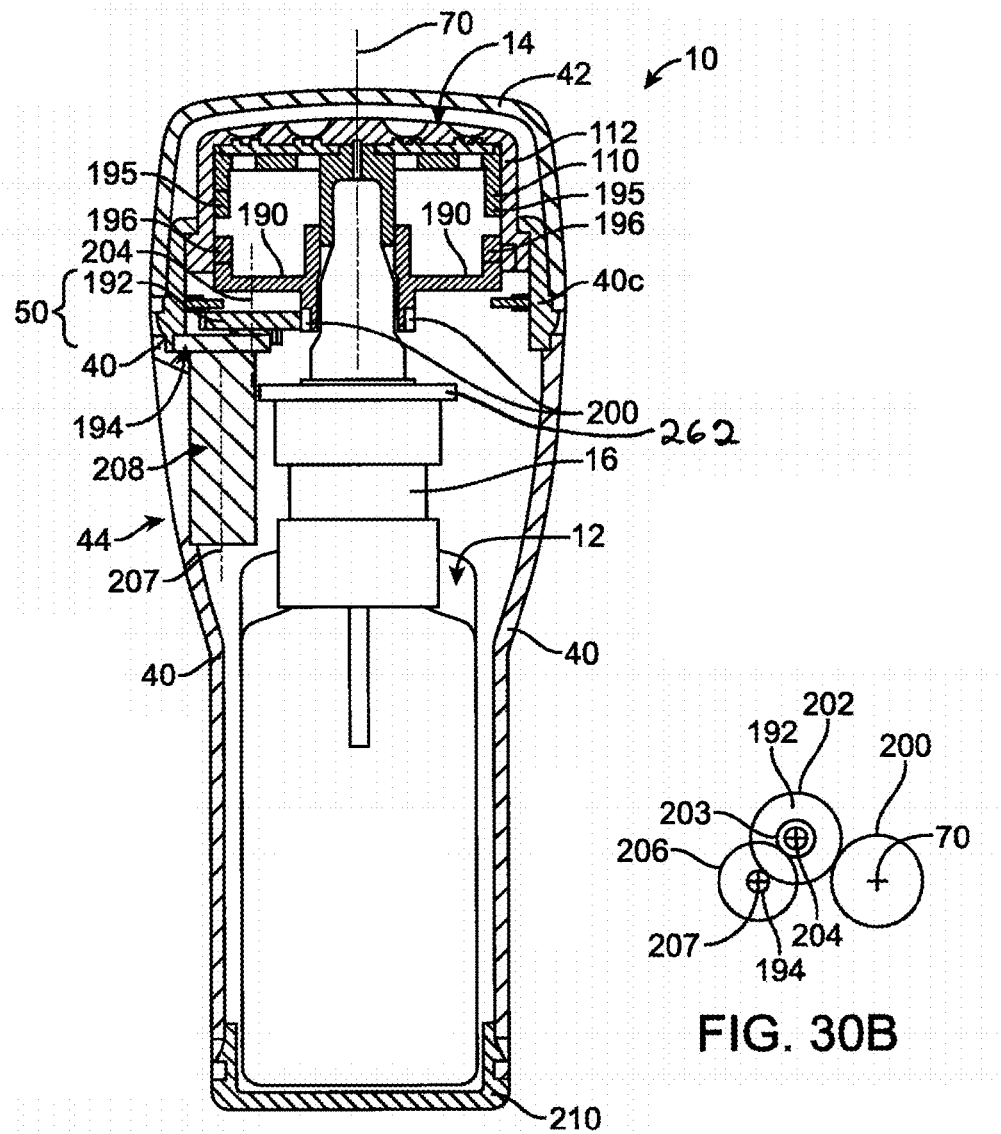
FIG. 30A
FIG. 30B
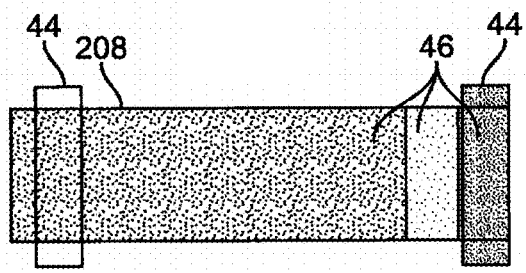
FIG. 30C

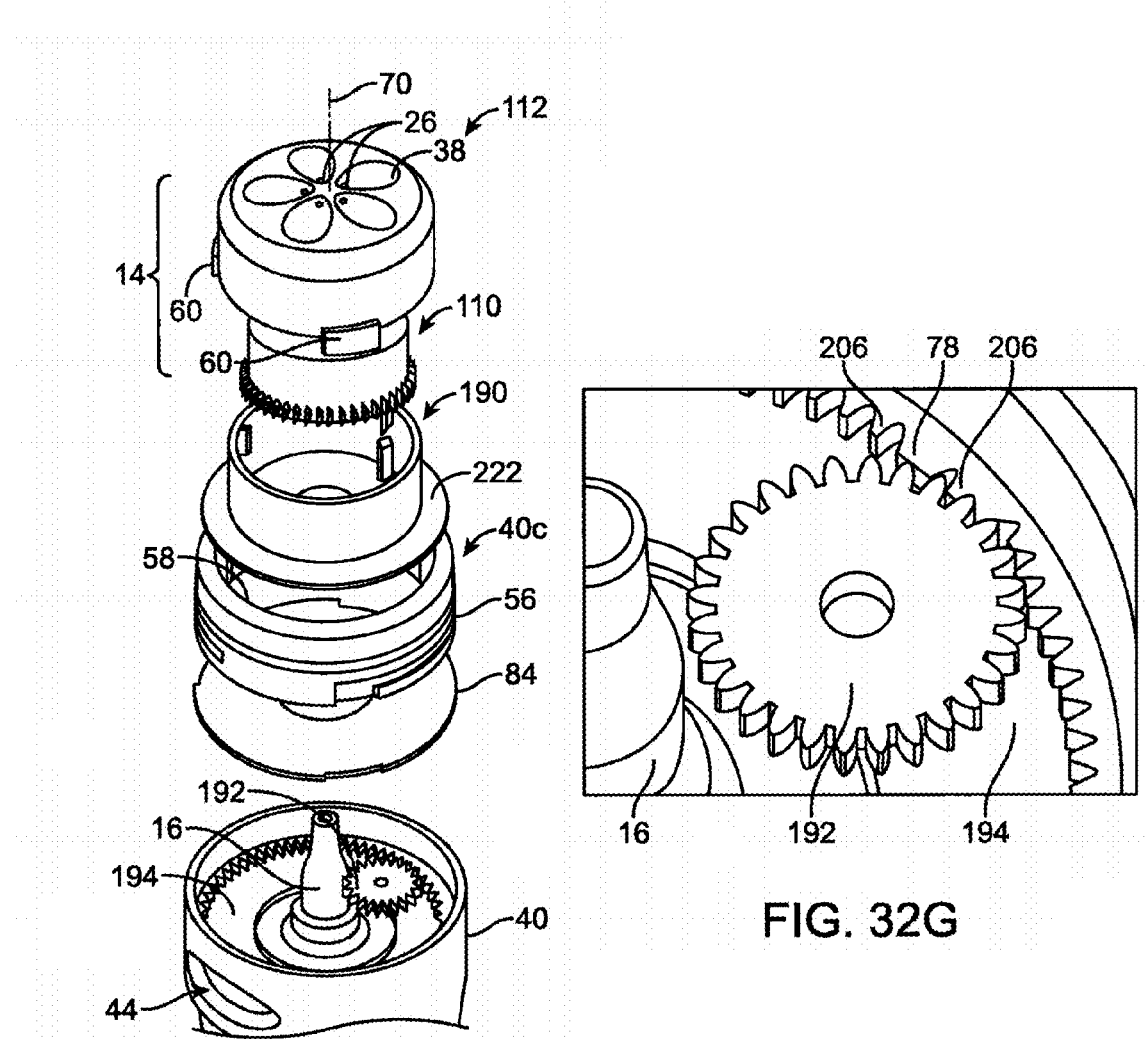

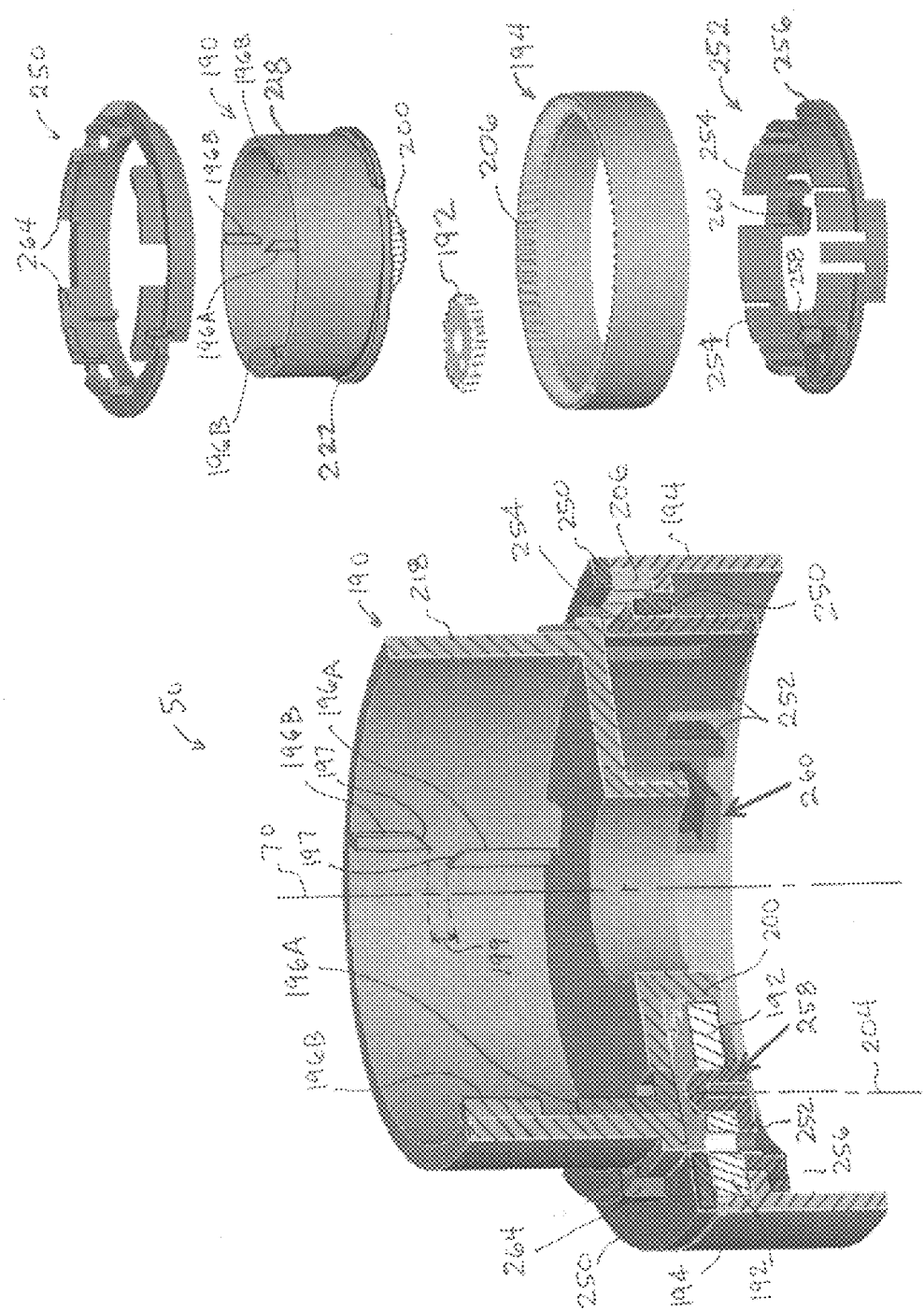

DEVICE AND METHOD FOR DISPENSING A DRUG

CROSS-REFERENCE TO RELATED APPLICATIONS

This application claims the benefit of U.S. Provisional Application No. 62/057,064, filed Sep. 29, 2014 and U.S. Provisional Application No. 62/108,344, filed Jan. 27, 2015, both of which are incorporated herein by reference in their entirety.

FIELD OF THE INVENTION

This invention relates generally to a device and method for dispensing a drug and, more particularly, to a device and method for dispensing a drug for topical administration.

BACKGROUND

Topical medications have been used to treat or prevent many conditions. For some medications, it is important to carefully control the amount of medication being applied to the skin to minimize unwanted side effects. Disposable sheets, wipes or pads have been used to apply topical medications. These topical applicators are made of absorbent material which carries the medication and wiping the skin treatment area with them allows for some transfer of medication. However, a significant amount of the medication can remain trapped in the absorbent material and thus be wasted. Also, the amount of medication that is transferred to the skin is highly dependent upon the technique of the user. For example, lightly pressing the pad on the skin will result in less drug transfer than using greater pressure and the amount of drug can also be dependent on the number of times the skin is wiped (with dose increasing with the number of passes). Moreover, the use of such absorbent material (or even other topical medications that are formulated as creams or lotions) also results in drug being transferred to the hands (whether it is the patient or caregiver) which could lead to excess exposure or inadvertent transfer to the administrator's eyes, mouth or other people.

Conventional applicator devices, such as roll-on balls, rub-on sticks and aerosol spray cans, can also present difficulty in controlling the amount of medication being applied to the skin. With such devices, the amount of medication dispensed can vary greatly day to day. For ball and stick applicators, the amount of medication dispensed can depend on the time duration at which the applicator is rolled or rubbed against the skin. For common aerosol spray cans, the amount of medication dispensed can depend on the time duration at which the nozzle valve is depressed by the user.

What is needed are a device and method that allows the user to control the amount and location of drug or active ingredient being dispensed so that a consistent and predictable amount is dispensed. Such control can prevent sub-effective dose from under-dosing as well as minimize waste of the drug and/or minimize unwanted side effects that may arise with excessive drug administration. What is also needed are a device and method for dispensing a drug that encourages the user to apply a prescribed or recommended dose of the drug.

SUMMARY

Briefly and in general terms, the present invention is directed to a device and method for dispensing a drug.

In aspects of the invention, a device for dispensing a drug comprises a case, a container, a pump, a spreader, and a lock. The container is disposed within the case and forms a chamber containing multiple doses of the drug. The pump is disposed on the container. The pump has a pump outlet and is configured to release the drug from the chamber and out of the pump outlet when the pump is actuated. The spreader is connected to and movable relative to the case. The spreader forms a drug passageway coupled to the pump outlet. The spreader is configured to actuate the pump as result of pressure applied to the spreader by a user of the device. The lock is connected to the spreader. The lock has a numerical limit and is configured to allow the spreader to actuate the pump when the pump has been actuated a number of times less than the numerical limit. The lock is further configured to prevent the spreader from actuating the pump when the pump has been actuated a number of times equivalent to the numerical limit.

Any one or a combination of two or more of the following optional aspects can be appended to the above aspect of the invention to form additional aspects of the invention.

In an aspect, the pump, when actuated by pressure applied to the spreader by the user, is configured to release a drug dose over a period of time or stroke distance and is configured to stop releasing the drug at the end of the period of time or stroke distance even when the pressure continues to be applied by the user to the spreader.

In an aspect, the spreader includes an outer surface configured to be pressed against the skin of the user, and the drug passageway has a plurality of outlets at the outer surface.

In an aspect, the lock is configured to move, with each actuation of the pump, irreversibly closer to a locked state at which the lock prevents the spreader from actuating the pump.

In an aspect, the lock includes a visual indicator having a starting position and an ending position, the starting position indicates that the spreader can actuate the pump, the ending position indicates that the spreader cannot actuate the pump, and the visual indicator is configured to move incrementally closer to the ending position each time the spreader actuates the pump.

In an aspect, the visual indicator has an intermediate position between the starting position and the ending position, and the intermediate position indicates that the pump can be actuated by the spreader a specified number of times (as set by the manufacturer) before the pump reaches the numerical limit and can no longer be actuated.

In an aspect, the spreader includes a first portion forming a flexible wall of the drug passageway, the flexible wall is configured to yield and allow a quantity of drug released from the chamber to pass through the drug passageway when the pump is actuated by the spreader and is configured to collapse and seal the drug passageway after the quantity of drug has passed through the drug passageway.

In an aspect, the spreader includes a second portion formed of a material that is less flexible than the first portion, and the drug passageway is disposed at an interface between the first portion and the second portion.

In an aspect, the first portion forms the outer surface of the spreader.

In an aspect, the spreader has a drug channel formed into the outer surface of the spreader, the drug channel has a depression and a ridge that surrounds and protrudes from the depression, and at least one outlet of the drug passageway is located at the depression of the drug channel.

In an aspect, the lock includes a lock member having a plurality of positions including a lockout position, the lock configured to move the lock member from one of the positions to the next position when the spreader actuates the pump, the lock member reaches the lockout position when the pump has been actuated to the numerical limit of the lock, and the lock member, when at the lockout position, obstructs movement of the spreader relative to the case and prevents the spreader from actuating the pump.

In an aspect, the lock includes a movable ratchet member configured to move incrementally relative to the case with each actuation of the pump by the spreader, and the lock member is attached to and moves with the movable ratchet member.

In an aspect, the movable ratchet member is a ring having a central space occupied by the container.

In an aspect, the lock further includes a spring, a slot, a ramp, and a plurality of teeth, the teeth are configured to move the lock member, a first tooth among the plurality of teeth is disposed inside the slot, and a second tooth among the plurality of teeth is disposed outside of the slot. The spreader is configured to move the teeth in a first direction such that first tooth moves out of the slot when the spreader actuates the pump. The spring is configured to move the teeth in a second direction opposite the first direction such that the second tooth slides on the ramp, which sliding causes the teeth to move in a third direction while moving in the second direction such that the second tooth moves comes to rest in the slot, wherein the third direction is different from the first direction and the second direction.

In an aspect, the lock includes a click mechanism configured to generate an audible click each time the spreader moves relative to the case by a distance that actuates pump to dispense a drug dose.

In an aspect, the lock includes a gate mechanism having a first condition and a second condition, the gate mechanism when at the first condition is configured to resist movement of the spreader when pressure applied to the spreader by the user is below a pressure threshold value needed to actuate the pump for release of a drug dose, the gate mechanism when at the second condition provides no resistance to movement of the spreader or provides reduced resistance to movement of the spreader as compared to the first condition, and the gate mechanism is configured to change from the first condition to the second condition when the pressure applied to the spreader by the user increases to a level at or above the pressure threshold value.

In an aspect, each drug dose is from 50 μL to 500 μL.

In an aspect, each drug dose is from 120 μL to 160 μL.

In an aspect, each drug dose includes glycopyrronium tosylate.

In an aspect, a maximum quantity of glycopyrronium tosylate in each drug dose is selected over the range of about 0.1 mg to about 100 mg.

In an aspect, the maximum quantity of glycopyrronium tosylate in each drug dose is selected over the range of about 1 mg to about 5 mg.

In an aspect, each drug dose includes glycopyrronium tosylate.

In an aspect, a maximum quantity of glycopyrronium tosylate in each drug dose is selected over the range of about 0.1 mg to about 100 mg.

In an aspect, the maximum quantity of glycopyrronium tosylate in each drug dose is selected over the range of about 1 mg to about 5 mg.

In aspects of the invention, a method comprises providing a device configured to release no more than a selected dose of glycopyrronium tosylate, and actuating the device to release no more than the selected dose of glycopyrronium tosylate, wherein the dose of glycopyrronium tosylate is selected over the range of about 0.1 mg to about 100 mg per day.

Any one or a combination of two or more of the following aspects can be appended to the above aspect of the invention to form additional aspects of the invention.

In an aspect, the device is configured to deliver a metered dose of glycopyrronium tosylate.

In an aspect, the device is configured for topical administration of the glycopyrronium tosylate.

In an aspect, the dose of glycopyrronium tosylate is selected over the range of about 1 mg to about 5 mg per day.

In an aspect, the dose of glycopyrronium tosylate is selected over the range of about 1 mg to about 2 mg per day.

In an aspect, the dose of glycopyrronium tosylate is provided in a drug solution.

In an aspect, the drug solution comprises alcohol, water, and a pH buffering agent.

In an aspect, the glycopyrronium tosylate is about 0.25% to 20% of the drug solution.

In an aspect, the alcohol:water ratio of the drug solution is selected over the range of 50:50 to 70:30.

In an aspect, the pH buffering agent is about 0.2% to 0.5% of the drug solution.

In an aspect, the pH buffering agent is citric acid/sodium citrate.

In an aspect, the pH of the drug solution is selected over the range of about 4.0 to 5.0.

In aspects of the invention, a device for dispensing a drug comprises a spreader for spreading the drug, the spreader including a first portion and a second portion, the first portion having a first portion upper surface and a first portion lower surface, the second portion having a second portion upper surface for applying the drug onto skin and a second portion lower surface, the second portion lower surface is disposed on and in contact with the first portion upper surface. A drug inlet is formed through the first portion lower surface. A drug passageway extends from the drug inlet to an aperture formed in the first portion upper surface. One or more drug outlets are formed through the second portion upper surface.

Any one or a combination of two or more of the following aspects can be appended to the above aspect of the invention to form additional aspects of the invention.

In an aspect, one or more grooves are formed into the first portion upper surface for conveying the drug toward the one or more drug outlets.

In an aspect, the second portion is a membrane, the second portion upper surface and the second portion lower surface are on opposite sides of the membrane, and the membrane is configured to inhibit or prevent leaks of the drug from the first portion in the absence of positive pressure in the drug passageway.

In an aspect, one or more annular drug channels are formed into the second portion upper surface for containing the drug discharged from the one or more drug outlets.

In an aspect, the device further comprises a container forming a chamber for containing multiple doses of the drug, a pump on the container, the pump having a pump outlet coupled to the drug inlet of the first portion of the spreader, the pump configured to release the drug from the chamber and out of the pump outlet when the pump is actuated, and optionally a lock connected to the spreader, the lock having a numerical limit and configured to allow the spreader to actuate the pump when the pump has been actuated a number of times less than the numerical limit, the lock further configured to prevent the spreader from actuating the pump when the pump has been actuated a number of times equivalent to the numerical limit.

In an aspect, the device further comprises a visual indicator for indicating completion of the doses of the drug contained in the chamber.

In an aspect, the visual indicator includes a numerical counter configured to change display of a number based on a total number of doses of the drug remaining in (or alternatively had been released by) the pump.

In an aspect, the visual indicator is configured to change display of a color based on a total number of doses of the drug released by the pump.

In aspects of the invention, a method for drug administration comprising the administration of a drug to the skin of a patient, wherein the drug is dispensed from the device of any one or a combination of aspects above.

In any of the aspects above, the drug is provided in a solution, suspension, gel, cream, lotion, or other form suitable for topical administration.

In any of the aspects above, the drug is in a liquid solution or suspension.

In any of the aspects above, the drug is in a gel.

In any of the aspects above, the drug is a cream for topical administration.

In any of the aspects above, the drug is a lotion for topical administration.

In any of the aspects above, the drug is an ointment for topical administration.

In any of the aspects above, the drug is a prescription medicine, an over-the-counter product, or any other substance for topical administration.

In any of the aspects above, the drug is: for the treatment of wrinkles, brown spots or surface roughness; an anesthetic; for the treatment of acne; for the treatment of psoriasis; for the treatment of skin ulcers; for the treatment of diabetic foot ulcers; for the treatment or prevention of baldness; for the treatment of infection; for the treatment of warts; for the treatment of dermatosis; for the treatment of tinea pedis, tinea versicolor, tinea cruris, tine corporis, jock itch or ringworm; for the treatment of dermatitis; for the treatment of rosacea; for the treatment of lice; for the treatment of actinic keratosis; for the treatment of varicose veins; for the treatment of cancer; for the treatment of onychomycosis; for treatment of hyperhidrosis; for the prevention of sunburn or UV protection; a deodorant or an antiperspirant.

In any of the aspects above, the drug is: sunscreen, hydrocortisone, steroid, tretinoin; benzocaine, butamben, dibucaine, lidocaine, oxybuprocaine, pramoxine, proparacaine, proxymetacaine, or tetracaine; erythromycin, benzoyl peroxide, clindamycin, penederm, sodium sulfacetamide, adapalene or Tazorac; alefacept or Tazorac; becaplermin; minoxidil; tigecycline, clindamycin or butenafine; podofilox; betamethasone; luliconazole, terbinafine or terbinafine hydrochloride; tacrolimus; azelaic acid; ivermectin; ingenol mebutate; polidocanol; mechlorethamine; efinaconazole; glycopyrronium bromide; glycopyrronium tosylate; or an aluminum salt.

In any of the aspects above, the drug is for administration to any region of the skin.

In any of the aspects above, the drug is for administration to: one or more axilla; one or more hands; one or more palms; one or more feet; one or more foot soles; the face; the forehead; the back; the lower back; the upper back; or to the genitals.

In an aspect of the invention, a device for dispensing a drug comprises a spreader for spreading a drug on the skin. The spreader includes a first portion including a first portion upper surface and a first portion lower surface, there being a first portion aperture formed through the first portion upper surface and configured to discharge the drug. The spreader includes a second portion including a second portion upper surface for applying the drug onto skin and a second portion lower surface, the second portion lower surface facing toward the first portion upper surface, there being a plurality of second portion apertures formed through the second portion upper lower surface and configured to receive the drug discharged from the first portion aperture, there being a plurality of drug outlets formed through the second portion upper surface and configured to discharge the drug received by the second portion apertures. The spreader includes a valve member disposed between the first portion and the second portion, the valve member configured to flex or bend from a first state to a second state in response to a change in hydraulic pressure on the valve member. The valve member, when in the first state, prevents or inhibits the drug from traveling from the first portion aperture to the drug outlets. The valve member, when in the second state, allows the drug to travel from the first portion aperture to the drug outlet.

In an aspect of the invention, a device for dispensing a drug comprises a case, a spreader for spreading a drug on the skin, the spreader extending out of the case. The device comprises a container for the drug, the container disposed within the case and including a pump configured to be actuated to deliver the drug to the spreader. The device comprises a lock within the case, the lock configured to prevent actuation of the pump when the pump has been actuated to a numerical limit of the lock. The lock includes a dose counter part coupled to the spreader. The dose counter part includes a visual indicator that is visible through an aperture in the case. The dose counter part rotates with axial movement of the spreader into the case. The rotation of the dose counter part moves the visual indicator within the aperture.

In an aspect of the invention, a device for dispensing a drug comprises a container for a drug, and a spreader connected to the container. The spreader has an exposed surface for spreading the drug on skin, the exposed surface including a plurality of drug outlets that dispense the drug from the container. The exposed surface further includes a plurality of concave drug channels arranged around a central axis of the spreader. At least some of the drug outlets are located within the drug channels. Each drug channel has an oval perimeter, the oval perimeter defined by a round narrow end, a round wide end, and a groove central region between the round narrow end and the round wide end. The round wide end has a radius of curvature greater than that of the round narrow end. The round narrow ends converge toward each other and are closer to the central axis than the round wide ends. Each drug channel has a depth that varies within the oval perimeter, the depth being greater at the groove central region than at the round narrow end and the round wide end.

In an aspect of the invention, a device for dispensing a drug comprises a spreader for spreading the drug, the spreader including a first portion and a second portion, the first portion having a first portion upper surface and a first portion lower surface, the second portion having a second portion upper surface for applying the drug onto skin and a second portion lower surface, the second portion lower surface is disposed on and in contact with the first portion upper surface. A drug inlet is formed through the first portion lower surface. A drug passageway extends from the drug inlet to an aperture formed in the first portion upper surface. At least one concave drug channel is formed in the second portion upper surface, each drug channel has a depth that varies, each drug channel includes a first groove region and a second groove region, the depth is greatest at the second groove region as compared to all other regions of the drug channel. A plurality of drug outlets are formed through the second portion upper surface, at least some of the drug outlets are located in the first groove region of the at least one concave drug channel, and none of the drug outlets present on the second portion upper surface are located in any second groove region on the second portion upper surface.

In an aspect of the invention, a device for dispensing a drug comprises a spreader for spreading the drug, the spreader including a first portion and a second portion, the first portion having a first portion upper surface and a first portion lower surface, the second portion having a second portion upper surface for applying the drug onto skin and a second portion lower surface, the second portion lower surface is disposed on and in contact with the first portion upper surface. A drug inlet is formed through the first portion lower surface. A drug passageway extends from the drug inlet to an aperture formed in the first portion upper surface. A plurality of drug outlets are formed through the second portion upper surface, and wherein the aperture formed in the first portion upper surface provides the drug to all the drug outlets, and none of the drug outlets are located directly above the aperture.

In an aspect of the invention, a device for dispensing a drug comprises a case, and a container within the case, the container forming a chamber containing multiple doses of the drug. The device further comprises a pump on the container, the pump having a pump outlet and configured to release the drug from the chamber and out of the pump outlet when the pump is actuated. The device further comprises a spreader connected to and movable relative to the case, the spreader forming a drug passageway coupled to the pump outlet, the spreader configured to actuate the pump as result of pressure applied to the spreader by a user of the device. The device further comprises a lock connected to the spreader, the lock having a numerical limit and configured to allow the spreader to actuate the pump when the pump has been actuated a number of times less than the numerical limit. The lock includes a lock member that changes position with each actuation of the pump by the spreader, the lock member is configured to prevent the spreader from actuating the pump when the pump has been actuated a number of times equivalent to the numerical limit.

In an aspect of the invention, a device for dispensing a drug comprises a case, and a container within the case, the container forming a chamber containing multiple doses of the drug. The device further comprises a pump on the container, the pump having a pump outlet and configured to release the drug from the chamber and out of the pump outlet when the pump is actuated. The device further comprises a spreader connected to and movable relative to the case, the spreader forming a drug passageway coupled to the pump outlet, the spreader including an exposed surface that, when pressed against the skin, actuates the pump to deliver the drug to the exposed surface. The device further comprises a lock connected to the spreader, the lock having a numerical limit and configured to allow the spreader to actuate the pump when the pump has been actuated a number of times less than the numerical limit. The lock includes a lock member that changes position with each actuation of the pump by the spreader, the lock member is configured to prevent the spreader from actuating the pump when the pump has been actuated a number of times equivalent to the numerical limit.

The features and advantages of the invention will be more readily understood from the following detailed description which should be read in conjunction with the accompanying drawings.

BRIEF DESCRIPTION OF THE DRAWINGS

FIGS. 1 and 2 are perspective section views partially showing exemplary devices for dispensing a drug.

FIG. 3 is a perspective view partially showing an exemplary spreader for topical application of a drug.

FIG. 6 is a perspective section view of the device of FIG. 4.

FIG. 7 is a cross-section view showing a lock within the device of FIG. 4 for limiting the total number of drug doses dispensed from the device.

FIGS. 9-11 are perspective views showing an exemplary sequence of steps for assembling the components of FIG. 8.

FIGS. 12A-12C are diagrams showing an exemplary sequence of steps in the function of a ratchet mechanism of a lock within the device of FIGS. 6-11.

FIG. 13 is a cross-section view showing an exemplary spreader for topical application of a drug.

FIG. 14 is a perspective view showing exemplary grooves (124) formed into a first portion (110) of a spreader.

FIGS. 15A and 15B are top views showing positions for drug outlets (26) in relation to the grooves of FIG. 14.

FIG. 16 is a cross-section view showing exemplary drug channels (38) formed in a second portion (112) of a spreader.

FIGS. 22-24A are perspective section views showing variously exemplary spreaders for topical application of a drug.

FIG. 28A is a section view showing an exemplary device for dispensing a drug.

FIG. 28B is a schematic view showing relationships between rotatable parts of a lock in the device of FIG. 28A.

FIG. 28C is a schematic view showing a portion of a dose counter part which would be visible through an aperture of the device of FIG. 28A.

FIG. 30A is a section view showing an exemplary device for dispensing a drug.

FIG. 30B is a schematic view showing relationships between rotatable parts of a lock in the device of FIG. 30A.

FIG. 30C is a schematic view showing a portion of a dose counter part which would be visible through an aperture of the device of FIG. 30A.

FIG. 32F is a perspective exploded view of components of FIG. 32A.

FIG. 32G is a detail view of an area of FIG. 32F.

FIG. 33A is a perspective section view showing rotatable parts of exemplary lock for use with any spreader herein.

FIG. 33B is a perspective exploded view of components in FIG. 33A.

DETAILED DESCRIPTION

Figure 5A:
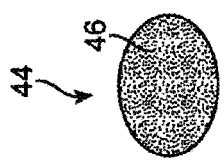
FIGS. 5A-5C are diagrams showing an exemplary visual indicator of drug doses remaining in a device for dispensing the drug.

Provided herein are devices and methods for the controlled topical administration of a drug by a user. The drug can be any drug that a patient or caregiver wishes to administer topically. In particular embodiments, the drug is provided in a solution, suspension, gel, cream, lotion, ointment, jelly, or other form suitable for topical administration. In certain embodiments, the drug is in a liquid solution or suspension. In certain embodiments, the drug is in a gel. The drug can be a prescription medicine, an over-the-counter product, or any other substance for topical administration.

In certain embodiments, the drug is for the treatment of wrinkles, brown spots or surface roughness. In certain embodiments, the drug is tretinoin. In certain embodiments, the drug is an anesthetic. In certain embodiments, the drug is benzocaine, butamben, dibucaine, lidocaine, oxybuprocaine, pramoxine, proparacaine, proxymetacaine, or tetracaine. In certain embodiments, the drug is for the treatment of acne. In certain embodiments, the drug is erythromycin, benzoyl peroxide, clindamycin, penederm, tretinoin, sodium sulfacetamide, adapalene or tazorac. In certain embodiments, the drug is for the treatment of psoriasis. In certain embodiments, the drug is alefacept or tazorac. In certain embodiments, the drug is for the treatment of skin ulcers such as diabetic foot ulcers. In certain embodiments, the drug is becaplermin. In certain embodiments, the drug is for the treatment or prevention of baldness. In certain embodiments, the drug is minoxidil. In certain embodiments, the drug is for the treatment of infection. In certain embodiments, the drug is tigecycline, clindamycin or butenafine. In certain embodiments, the drug is for the treatment of warts. In certain embodiments, the drug is podofilox. In certain embodiments, the drug is for the treatment of dermatosis. In certain embodiments, the drug is betamethasone. In certain embodiments, the drug is for the treatment of *tinea pedis, tinea versicolor, tinea cruris*, tine corporis, jock itch or ringworm. In certain embodiments, the drug is luliconazole, terbinafine or terbinafine hydrochloride. In certain embodiments, the drug is for the treatment of dermatitis. In certain embodiments, the drug is tacrolimus. In certain embodiments, the drug is for the treatment of rosacea. In certain embodiments, the drug is azelaic acid. In certain embodiments, the drug is for the treatment of lice. In certain embodiments, the drug is ivermectin. In certain embodiments, the drug is for the treatment of actinic keratosis. In certain embodiments, the drug is ingenol mebutate. In certain embodiments, the drug is for the treatment of varicose veins. In certain embodiments, the drug is polidocanol. In certain embodiments, the drug is for the treatment of cancer. In certain embodiments, the drug is mechlorethamine. In certain embodiments, the drug is for the treatment of onychomycosis. In certain embodiments, the drug is efinaconazole.

In certain embodiments, the drug is for treatment of hyperhidrosis. In certain embodiments, the drug is glycopyrrolate or glycopyrronium bromide. In certain embodiments, the drug is glycopyrronium tosylate. In certain embodiments, the drug is an antiperspirant, for instance an aluminum salt.

The devices and methods can be for administration to any region of the skin. In particular embodiments, the administration is to one or more axilla. In particular embodiments, the administration is to one or more hands. In particular embodiments, the administration is to one or more palms. In particular embodiments, the administration is to one or more feet. In particular embodiments, the administration is to one or more foot soles. In particular embodiments, the administration is to the face. In particular embodiments, the administration is to the forehead. In particular embodiments, the administration is to the back. In particular embodiments, the administration is to the lower back. In particular embodiments, the administration is to the upper back. In particular embodiments, the administration is to the genitals.

Referring now in more detail to the drawings for purposes of illustrating exemplary embodiments of the invention, wherein like reference numerals designate corresponding or like elements among the several views, there is shown in FIG. 1 device 10 for dispensing a drug for topical administration.

Device 10 comprises container 12 and spreader 14. Container 12 contains a drug and includes pump 16 configured to discharge the drug into spreader 14. Spreader 14 is configured to carry the discharged drug and then to spread the drug on the skin.

To dispense the drug, a user of device 10 presses outer surface 18 of spreader 14 against an area of the skin on which the drug is to be applied. Mechanical pressure on outer surface 18 is transmitted by spreader 14 to pump 16. The direction of pressure or force is depicted by arrows 20. The pressure actuates pump 16 to release the drug from within chamber 22 of container 12. When released from chamber 22, the drug travels through pump 16 and into drug passageway 24 within spreader 14. Drug passageway 24 extends to outer surface 18 where the drug exits device 10 and makes contact with the skin. The user may slide spreader 14 back and forth and/or in a circular motion against the skin to spread the drug on the skin.

In FIG. 1, drug passageway 24 has a plurality of outlets 26 formed through outer surface 18 of spreader 14. Outlets 26 are spaced apart across a flat expanse of outer surface 18. Due to the distance between outlets 26, the drug could be dispersed over a wider area of spreader 14 as it exits device 10 as compared to a spreader with only a single outlet. With the spreader configuration of FIG. 1, Applicants have found that the drug is evenly dispersed across the flat expanse of the spreader 14. In some instances, however, some of the drug escapes from peripheral edge 30 of spreader 14, where it accumulates when spreader 14 is pressed against the skin. If the drug accumulates beyond peripheral edge 30, it may be possible for significant quantities of the drug to drip down sides 39 of spreader 14 instead of being spread on the user's skin. In particular embodiments, the spreader configuration of FIG. 1 is useful for a drug that is sufficiently viscous to minimize drug escape.

In FIG. 2, drug passageway 24 has only a single outlet 26. Drug channel 38 is formed into outer surface 18. Drug channel 38 has depression 34 and ridge 36 that surrounds and protrudes from depression 34. An annular depression, referred to as drug channel 38, surrounds ridge 36. Outlet 26 is located at depression 34. Depression 34 and ridge 36 form a central cup in which the drug is carried immediately after it exits device 10. With this spreader configuration, Applicants have found that when spreader 14 is pressed on the skin, some of the drug escapes from the central cup and is captured in drug channel 38, which makes it less likely for the drug to drip down sides 39 of spreader 14 and more likely that the entire drug dose will be used to uniformly coat the treatment area of the skin. In certain embodiments, drug channel 38 is useful for a drug that is less viscous and likely to escape in the absence of drug channel 38.

In other embodiments, the spreader configuration of FIG. 2 is modified so that drug passageway 24 has multiple outlets (see e.g., FIG. 3). The outlets are located at depression 34. Optionally, additional outlets are located at drug channel 38.

In FIGS. 1 and 2, the forward facing area of spreader 14 is defined as the surface area enclosed within peripheral edge 30. In plan view, the forward facing area is a circle and peripheral edge 30 has a diameter of 45 mm. The plan view refers to the view of the forward facing area in the direction of arrow 20. Other diameters can be implemented, such as 35 mm. The diameter of peripheral edge 30 can depend on various factors such as the volume of the drug dose which is to be applied and the expected size of the skin treatment area. For example, a larger diameter can be implemented for device 10 designed for adults as to compared to one designed for young children. Also, the diameter of peripheral edge 30 can be miniaturized (e.g., 5-10 mm) for microdosing for applications where lower doses are desired (e.g., applications for warts or around eye areas and the like).

In FIG. 2, depression 34, ridge 36, and drug channel 38 each forms a circle when seen in plan view. The circles formed by ridge 36 and drug channel 38 are concentric. The forward facing area, depression 34, ridge 36, and drug channel 38 can have shapes other than circles in order to facilitate application of the drug on a skin treatment area which may not be circular or flat.

As shown in FIG. 3 for example, the forward facing area, depression 34, ridge 36, and drug channel 38 are elliptical in plan view, i.e, when viewed in the direction of arrow 21. The elliptical shapes can facilitate application of the drug on an elongate, non-circular skin treatment area. Also, spreader 14 has an overall convex shape in elevation, i.e., when viewed from the side in the direction of arrow 23. The overall convex shape can facilitate application of the drug on a concave treatment area, such as the axilla or armpit of the user.

The depth and surface area of depression 34 and drug channel 38 may depend on various factors. One potential factor is the volume of the drug dose which is to be carried on the forward facing area of spreader 14 prior to spreading the drug on the skin. For example, a greater depth and surface area would be needed for a drug dose of 250 µL as compared to that needed for a drug dose of 140 µL.

In FIG. 3, only a single ridge 36 and a single drug channel 38 are labeled. It will be appreciated that more ridges and drug channels can be implemented in a concentric arrangement. The number of ridges and drug channels may depend upon the area size of spreader 14, the amount of drug dispensed with each actuation of pump 16, and/or the viscosity of the drug composition. A greater amount of drug and/or a lower viscosity may call for a greater number to prevent escape of the drug beyond peripheral edge 30 of spreader 14. Spreader 14 can have only a single ridge, or it can have 2, 3, 4, 5, or more ridges which are concentric which each other. Spreader 14 can have only a single drug channel, or it can have 2, 3, 4, 5, or more drug channels which may be arranged in any manner (e.g., are concentric which each other). Each drug channel can be bounded by a pair ridges such that an inner boundary of the drug channel is defined by one of the ridges, and an outer boundary of the drug channel is defined by another one of the ridges.

Pump 16 is configured to be actuated multiple times. The amount released with each actuation of pump 16 is referred to as a drug dose. The drug dose can be a solution that comprises the drug (i.e., the active ingredient) and other ingredients such as alcohol, water, and a pH buffering agent. With each actuation of pump 16, the drug dose should be about the same so that the user can have confidence in the amount of drug being applied to the skin. For example, the drug dose released from the first actuation of pump 16 should be about the same as the drug dose released from the tenth, twentieth, and thirtieth actuation of pump 16. In this context, the phrase "about the same" means within 20% of an average drug dose. The dispensing tolerance of 20% can be smaller, such as 15%, 10%, or 5% in particular embodiments. For example, pump 16 can be configured to release an average drug dose of 140 µL when actuated. So that the drug dose is about the same with each actuation, pump 16 can be configured to have a dispensing tolerance of 15% around 140 µL so that each actuation of pump 16 will dispense a drug dose from about 120 µL to about 160 µL.

The average drug dose can be other than 140 µL. For example, the average drug dose can be 50 µL, 100 µL, 250 µL, 500 µL or other quantity. The average drug dose can depend upon the size of the skin surface area that is expected to be treated with each actuation of pump 16. The average drug dose can also depend upon the quantity or concentration of the drug (i.e, the active ingredient) in the drug dose. In cases where the active ingredient is glycopyrronium tosylate, the glycopyrronium tosylate can be from 0.25% to 2%, from 0.25% to 3%, from 0.25% to 4%, from 0.25% to 5%, from 0.25% to 6%, or from 0.25% to 20% of the drug dose. In cases where the drug dose is a solution that includes alcohol, water, and a pH buffering agent, the alcohol:water ratio of the solution can be in the range of 50:50 to 70:30. The pH buffering agent can be 0.2% to 0.5% of the solution. The pH buffering agent can be citric acid/sodium citrate. The pH of the solution can be from 4.0 to 5.0.

When actuated by pressure applied to spreader 14 by the skin treatment area on the user, pump 16 will release the drug dose over a limited period of time or stroke distance, such that release of the entire drug dose occurs relatively quickly. Alternatively, the time period can from 0.1 second to 1 second, or from 0.1 second to 0.5 second. After the entire drug dose is released, it can then be distributed evenly across the entire skin treatment area when the user continues to press and slide spreader 14 against the skin. Since spreader 14 is pressed against the skin during the distribution process, it is desirable for pump 16 to stop releasing the drug even when the user continues to apply pressure to spreader 14 (to enable a metered dose).

Various configurations for pump 16 can be implemented. For example, pump 16 can have a nozzle at the exterior of pump 16. The nozzle is firmly held by a fixture over an opening of container 12. The nozzle has an outlet from which the drug is dispensed. The nozzle outlet is coupled to drug passageway 24 of spreader 14. The nozzle can be attached to a movable piston within pump 16. When the user presses spreader 14 against the skin treatment area, spreader 14 pushes the nozzle, and the piston produces suction that draws the drug into a dip tube within chamber 22 and then out of the nozzle outlet. A pump spring within pump 16 is compressed when spreader 14 pushes the nozzle. Thereafter, the pump spring returns the nozzle to its starting position.

Figure 4:
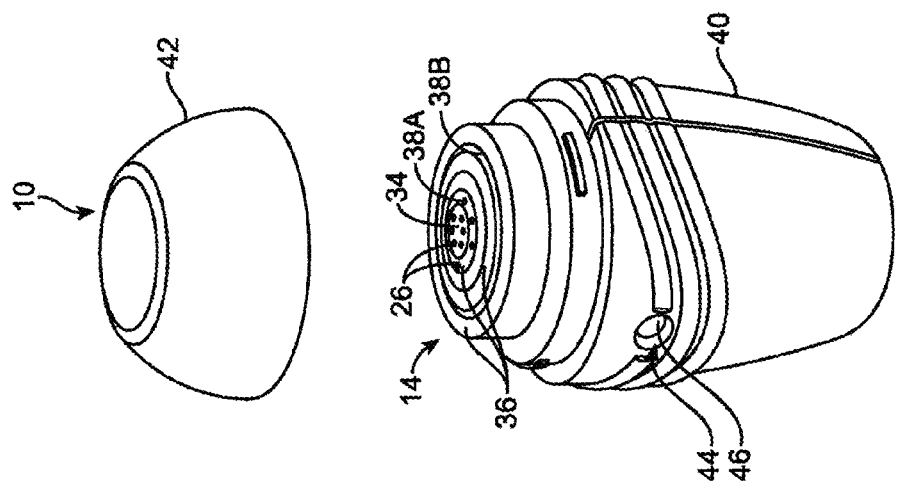
FIG. 4 is a perspective view showing an exemplary device for dispensing a drug.

Device 10 can be configured as shown in FIG. 4. Device 10 comprises case 40 and cover 42. Case 40 carries container 12 which is hidden from view. Spreader 14 is connected to and movable relative to case 40. Cover 42 is removably attached to case 40 to protect spreader 14 from dust and contamination. Cover 42 is removed and reattached to case 40 by the user. Cover 42 is detached from case 40 when the drug is being applied by spreader 14 to the skin treatment area. After the drug is applied, cover 42 can be reattached to case 40 to keep spreader 14 clean and to prevent it from accidentally dispensing drug when depressed. Cover 42 can have any of screw features or snap features for attaching it to case 40.

Various drug channel designs can be used to hold the liquid volume and prevent it from dripping before it can be spread onto the surface of the skin. For example, one such design is shown in FIG. 4 where central depression 34, three ridges 36, and two drug channels 38A and 38B are formed on the forward facing area of spreader 14. Drug passageway 24 has a plurality of branches (hidden from view) that lead to outlets 26 on the forward facing area of spreader 14. Outlets 26 are located in central depression 34 and inner drug channel 38A.

Device 10 is designed to allow only a limited number of drug doses to be released. The numerical limit can correspond to when the drug contents of container 12 is expected to be nearly depleted. When the numerical limit is reached, pump 16 (hidden from view in FIG. 4) cannot be actuated again, which thereby reduces the possibility that an incomplete drug dose will be released due to an insufficient quantity within container 12. The numerical limit can be established by a lock built into device 10. The lock has an unlocked state and a locked state. The lock is capable of moving from the unlocked state to the lock state but not from the lock state to the unlocked state. The lock is configured, when in the unlocked state, to allow spreader 14 to actuate pump 16 when pump 16 has been actuated a total number of times less than a numerical limit. The lock is configured, when in the locked state, to prevent spreader 14 from actuating pump 16 when pump 16 has been actuated a number of times equivalent to the numerical limit. The lock changes from the unlocked state to the locked state when the user of device 10 actuates pump 16 to the numerical limit. The lock is configured such that the user cannot move the lock from the locked state to the unlocked state.

Aperture 44 is formed through an outer wall of case 40 to expose visual indicator 46 which is attached to or forms a part of the lock. Visual indicator 46 can indicate completion of the doses of the drug contained in chamber 22 of container 12. Visual indicator 46 informs the user of whether the lock is approaching or is at the locked state. Visual indicator 46 includes a graphical marker, such as a number, line or colored bar or other symbol, which changes position incrementally within aperture 44 as the total number of times pump 16 is actuated approaches the numerical limit. For example, visual indicator can be configured to change display of a color based on a total number of doses of the drug remaining in pump 16, as shown in FIGS. 5A-5C.

Figure 5B:
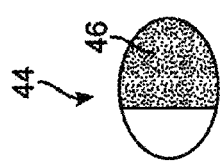
Figure 5C:
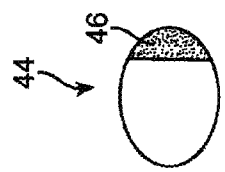

In FIG. 5A, visual indicator 46 begins to appear in aperture 44 when pump 16 can be actuated only a finite number of times before the lock changes to the locked state. When the user actuates pump 16 one or more times, visual indicator 46 changes position by moving to the left as shown in FIG. 5B. When the user again actuates pump 16 one or more times, visual indicator 46 changes position by moving further to the left as shown in FIG. 5C.

For example, the visual indicator position illustrated in FIG. 5A can inform the user that pump 16 can be actuated 2 more times, 6 more times, or 12 more times before the lock changes to the locked state. The visual indicator position illustrated in FIG. 5B can inform the user that pump 16 can be actuated only 1 more time, 3 more times, or 6 more times before the lock changes to the locked state. The visual indicator position illustrated in FIG. 5C can inform the user that pump 16 has been actuated to the numerical limit and that the lock is now in the locked state which prevents pump 16 from ever being actuated again.

Alternatively, the position of visual indicator 46 shown in FIG. 5A can correspond to four remaining actuations of pump 16. This can inform the user that device 10 can be used for a specified number of times (e.g., for only two more days to provide one drug dose at each axilla per day). Also, the position of visual indicator 46 shown in FIG. 5B can correspond to two remaining actuations of pump 16. For example, this can inform the user that device 10 can be used for only one more day to provide one drug dose at each axilla.

Visual indicator 46 can be a numerical counter configured to change display of a number based on a total number of doses of the drug dispensed or number of doses remaining in pump 16. For example, Visual indicator 46 can be a series of printed numbers in ascending order so that a particular number appears through aperture 44 to indicate the current total number of times pump 16 has been actuated. With each actuation of pump 16, visual indicator 46 shifts position so that the next higher number moves into aperture 44. Alternatively, the printed numbers can be in descending order so that a particular number appears through aperture 44 to indicate the remaining number of times the pump 16 can be actuated. With each actuation of pump 16, visual indicator 46 shifts position so that the next lower number moves into aperture 44.

Visual indicator 46 has a starting position and an ending position. Visual indicator 46 is at the starting position when no drug doses have been dispensed from device 10. Visual indicator 46 is at the ending position (FIG. 5C) when the numerical limit of drug doses have been dispensed from device 10 and pump 16 cannot be actuated. Visual indicator 46 includes one or more intermediate positions between the starting position and the ending position. Any one of the positions of visual indicator 46 illustrated in FIGS. 5A and 5B can be an intermediate position that indicates that pump 16 can be actuated by the spreader only one or two more times before the lock reaches its numerical limit.

The lock sets the numerical limit on the total number of times pump 16 can be actuated. The lock can be configured to establish a numerical limit of 30, 60, 120, or more. The lock can be configured to establish a numerical limit that is at least 30, at least 60, or at least 120 drug doses. Other numerical limits can be implemented. In cases where device 10 is intended for use in treating two skin treatment areas of the user per day (e.g., both axilla of the user per day), it can be desirable for the numerical limit to be an even number such as 20, 22, 24 and so on. The numerical limit can depend upon the volumetric capacity of chamber 22 of container 12. The numerical limit can depend upon the desired duration of treatment.

For example, the numerical limit can be 60 drug doses when a prescribed treatment calls for a single drug dose per day at each axilla of the user for 30 days. Each drug dose from a single actuation of pump 16 can contain a quantity of glycopyrronium tosylate. The quantity can be within the range of 0.5 mg to 5 mg, 0.1 to 100 mg, 0.5 mg to 10 mg, or 1 mg to 5 mg, or 1 mg to 2 mg.

As a further example, the numerical limit can be 120 drug doses so that device 10 can be used to dispense four drug doses per day (e.g., two drug doses per axilla per day) for 30 days. Each drug dose can contain half the quantity of glycopyrronium tosylate in the previous example, so that when actuating pump 16 twice at each axilla, the user applies a quantity that is within the range of 0.1 mg to 100 mg, 0.5 mg to about 10 mg per axilla per day, or 1 mg to 5 mg per axilla per day, or 1 mg to 2 mg per axilla per day.

When treating other body parts, the quantity of glycopyrronium tosylate dispensed can be as in the examples above, or can be less or greater than the examples above.

Figure 8:
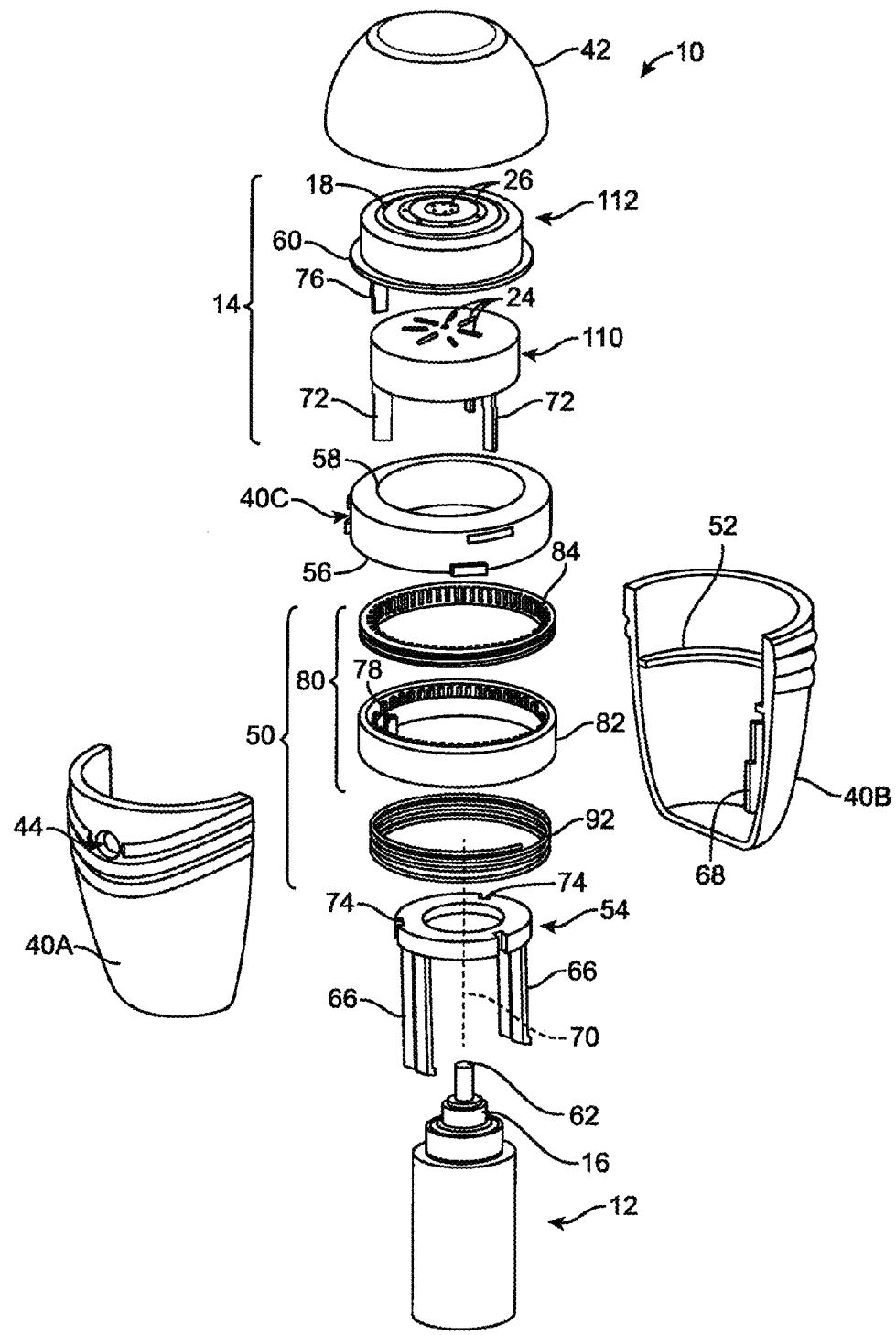
FIG. 8 is a perspective exploded view of exemplary components of the device of FIG. 4.

FIGS. 6-8 show an exemplary construction of device 10. Components of lock 50 are contained within case 40. Case 40 comprises three distinct parts: case sides 40A and 40B and case top 40C. The distinct parts facilitate manufacturing and assembly. First, case sides 40A and 40B are joined together to form a compartment as shown in FIG. 9. Case sides 40A and 40B can be joined permanently, such as with an adhesive, ultrasonic welding, or molded in a single piece. Lock 50 is placed into the compartment as shown in FIG. 10. Lock 50 rests on top of platform 52 (FIG. 8) firmly attached to each of case sides 40A, 40B. Next, container 12, container holder 54, and spreader 14 are assembled together to form a subassembly that is then placed in the compartment as shown in FIG. 11. Thereafter, case top 40C is secured onto case sides 40A, 40C. Case top 40C can be secured permanently such as with an adhesive, ultrasonic welding, or mechanical features.

When fully assembled, bottom edge 56 of case top 40C engages the top of lock 50 so as to prevent lock 50 from lifting out of the compartment. Spreader 14 extends through a central opening of case top 40C and is capable of moving up and down relative to case top 40C and container 12. Inner lip 58 of case top 40C engages flange 60 of spreader 14 so as to prevent spreader 14 from separating away from pump 16 of container 12.

Container holder 54 aligns pump outlet 62 (FIG. 6) of pump 16 with drug passageway inlet 64 of spreader 14. Container holder 54 includes rails 66 (FIG. 8) that engage ribs 68 firmly attached to on each of case sides 40A, 40B. Rails 66 and ribs 68 restrict or prevent container holder 54 and spreader 14 from rotating about central axis 70 relative to case parts 40A, 40B, and 40C. Spreader 14 includes guide members 72 which are slidingly received within slots 74 formed in container holder 54. Guide members 72 and slots 74 restrict or prevent spreader 14 from rotating about central axis 70 relative to container holder 54. Guide members 72 allow spreader 14 to move axially relative to container 12 in a direction parallel to central axis 70.

Pressure applied by the user on the forward facing area of spreader 14 results in axial movement of spreader 14 which actuates pump 16 of container 12 to force the drug into fluid passageway 24 of spreader 14. Spreader 14 includes rigid leg 76 (FIGS. 7 and 8) that moves into lock 50 during axial movement of spreader 14. When leg 76 moves into lock 50, lock 50 advances one step toward its locked state. Lock 50 is configured to advance by a total number of steps that corresponds to the total number of drug doses which device 10 is designed to deliver. The total number of steps establishes the numerical limit, previously described above, at which pump 16 can no longer be actuated by spreader 14.

Lock 50 includes lock member 78 (FIGS. 7 and 8) which moves incrementally with each step taken by lock 50. Lock member 78 moves closer to its lockout position with each step of lock 50 that results from axial movement of spreader 14 and from actuation of pump 16. When not at the lockout position, lock member 78 is not located directly above ledge 81 (FIG. 7) firmly attached to case side 40A, and lock member 78 is capable of moving up and down due to axial movement of spreader 14. Thereafter, when at the lockout position, lock member 78 is located directly above ledge 81. When the user of device 10 attempts to actuate pump 16 again, lock member 78 abuts ledge 81 so as to obstruct and prevent axial movement of spreader 14 relative to container 12. This prevents pump 16 from being actuated by spreader 14.

Lock 50 includes two-part ring 80 (FIG. 8) having a ratchet mechanism configured to rotate first ring 82 of the two-part ring each time spreader 14 actuates the pump 16. When leg 76 of spreader 14 moves into lock 50, leg 76 engages first ring 82 so that first ring 82 moves one step toward the numerical limit of lock 50. With each step, first ring 82 incrementally rotates in a first rotational direction relative to second ring 84 of the two-part ring. Second ring 84 is concentric with first ring 82 and prevents rotation of first ring 82 in the opposite rotational direction. Lock member 78 is firmly attached to and rotates with first ring 82. Each incremental rotational of first ring 82 causes lock member 78 to move closer to its lockout position directly above ledge 81 (FIG. 7). Visual indicator 46 (FIGS. 5A-5C) can be a graphic marker on first ring 82.

First and second rings 82, 84 are interlocking ratchet members that each forms a closed circle having a central opening. The central opening provides a space which is occupied by pump 16, thereby allowing for an efficient use of space within the confines of case 40. Although the interlocking ratchet members (in the form rings 82, 84) are illustrated as closed circles encompassing 360 degrees, it will be appreciated that the interlocking ratchet members can each be configured as an arc of less than 360 degrees. For example, rings 82, 84 (non-limiting examples of interlocking ratchet members) can be replaced with half circles each of which forms a 180 degree arc or with three-quarter circles each of forms a 270 degree arc.

First ring 82 rotates incrementally relative to case 40 and second ring 84 with each actuation of pump 16. Second ring 84 is firmly attached to case 40. Second ring 84 remains stationary in that it does not rotate relative to case 40 with each actuation of pump 16. First ring 82 can be referred to as a movable ratchet member, and second ring 84 can be referred to as a fixed ratchet member. The movable and fixed ratchet members need not be circles and need not have an overall arc shape. Instead, the ratchet members can extend in a straight line, in which case the movable ratchet member can move incrementally in a straight line relative to case 40 with each actuation of pump 16.

A movable ratchet member—which can be a ring (e.g., first ring 82), arc-shaped or linear—can be longer in length than the fixed ratchet member. Since the movable ratchet member moves incrementally relative to case 40 with each actuation of pump 16, the length of movable ratchet member can depend on the total number of drug doses which device 10 is designed to dispense.

An exemplary ratchet mechanism for the lock can take the form of a plurality of angled teeth 86 and ramps 88 as shown in FIGS. 12A to 12C. Teeth 86 are firmly attached to movable ratchet member 82 which moves relative to case 40 with each actuation of pump 16. Lock member 78 (FIGS. 7 and 8) is firmly attached to and moves with movable ratchet member 82. The movable ratchet member can be first ring 82 illustrated in FIG. 8 or another component, such as an arc-shaped movable ratchet member or linear movable ratchet member.

Ramps 88 are firmly attached to fixed ratchet member 84. Fixed ratchet member 84 is firmly attached to case 40 and does not move relative to case 40 with each actuation of pump 16. The fixed ratchet member can be second ring 84 illustrated in FIG. 8 or another component, such as an arc-shaped fixed ratchet member or linear fixed ratchet member. The function of teeth 86 and ramps 88 is the same for ratchet members that are rings, arcs, or linear.

In FIG. 12A, first tooth 86A is disposed inside slot 89 between ramps 88. Second tooth 86B is disposed outside of slot 89. Leg 76 of spreader 14 pushes movable ratchet member 82 together with all teeth 86 in first direction 90 when spreader 14 moves axially due to pressure applied on the forward facing area of spreader 14 by the skin treatment area of the user. Consequently, first tooth 86A moves out of slot 89.

In FIG. 12B, leg 76 has stopped moving and is held in place by continued pressure applied on the forward facing area of spreader 14 by the skin treatment area of the user. Spring 92 (FIG. 7) urges movable ratchet member 82 together with all teeth 86 to move in second direction 94 opposite first direction 90. Spring 92 can be a helical spring as illustrated or another type of spring such as a leaf spring. Because teeth 86 are now disengaged from ramps 88, second tooth 86B slides off of angled surface 96 of leg 76 due to action of spring 92.

As shown in FIG. 12C, the sliding motion between second tooth 86B and angled surface 96 of leg 76 causes movable ratchet member 82 and lock member 78 (FIGS. 7 and 8) to move in third direction 100 while simultaneously moving in second direction 94. The combination of movement in the second and third directions will cause second tooth 86B to eventually move into slot 89 which was previously occupied by first tooth 86A. Movement of second tooth 86B into slot 89 corresponds to one step toward the numerical limit of lock 50. When second tooth 86B comes to rest within slot 89, second tooth 86B is trapped and moveable ratchet member 82 is held in place until the user releases spreader 14 and depresses spreader 14 again.

If movable ratchet member 82 is a ring (e.g., first ring 82 in FIG. 8) or is arc-shaped, third direction 100 can be clockwise rotation as viewed along central axis 70 and looking down on the outer surface of spreader 14. The inclination angle of angled surfaces 96, teeth 88, and ramp surfaces 98 can be altered from what is shown in FIGS. 12A-12C so that third direction 100 can be counterclockwise rotation.

Pump 16 ensures that leg 76 is at its starting position shown in FIG. 12A when no pressure is applied by the user on the forward facing area of spreader 14. Spring 92 ensures that teeth 86 are engaged with ramps 88 as shown in FIG. 12A when no pressure is applied by the user on the forward facing area of spreader 14. Distance 102 is the axial distance by which spreader 14 must travel so that lock 50 advances irreversibly by one step toward the numerical limit of lock 50. Distance 102 can be measured from trailing edge 104 of leg 76 at the starting position (FIG. 12A) to the leading edge 106 of ramps 88. Distance 108 is the axial distance by which pump 16 must be displaced or actuated to release a full drug dose. The full drug dose can be one that is within a certain range, such as an average drug dose plus/minus a dispensing tolerance as previously described above. The full drug dose can be one that contains a quantity of glycopyrronium tosylate that is within the range of 0.1 mg to 100 mg, 0.5 mg to 10 mg, or 1 mg to 5 mg, or 1 mg to 2 mg.

For example, distance 102 can be 5 mm in a case where complete actuation of pump 16 requires pump 16 to be pushed at least 5 mm. This will help ensure that when leg 76 is at its final, fully depressed position (FIG. 12B), lock 50 will reliably advance one step in the manner previously described, and pump 16 will have been completely actuated to release the full drug dose. Other values for distance 102 can be implemented, such as 10 mm and 15 mm.

The term "lock stroke length" is the distance 102 by which spreader 14 must travel so that lock 50 advances irreversibly by one step toward the numerical limit of lock 50. Distance 108 (FIGS. 12A and 12B) is the maximum difference in the starting and final positions of spreader 14 when the user depresses spreader 14. The arrangement of parts within device 10 determines distance 108. For example, the starting position of spreader 14 can correspond to when inner lip 58 (FIG. 8) of case top 40C abuts flange 60 of spreader 14, and the final position of spreader 14 can correspond to when movable ratchet member 82 abuts platform 52 (FIG. 8) on case 40. Alternatively, the final position of spreader 14 can correspond to when pump 16 has reached its limit of axial movement. The term "pump stroke length" is the minimum distance P for completely actuating pump 16 so that it dispenses a full drug dose. The pump stroke length P can be any distance from distance 102 to distance 108. For example, pump stroke length P can be 5 mm, 7 mm, 12 mm, or another value.

In some embodiments, lock stroke length 102 is less than the pump stroke length P. With this configuration, lock 50 will advance irreversibly even when spreader 14 is not fully depressed. For example, lock stroke length 102 can be 50%, 60%, or 70% of P. The user may be discouraged from attempting to dispense a partial drug dose since lock 50 will advance regardless of whether spreader 14 is depressed to release a partial drug dose or the full drug dose.

Device 10 includes a click mechanism that helps the user determine when spreader 14 has been depressed by an axial distance that causes complete actuation of pump 16 for delivery of a full drug dose. The click mechanism generates a click when axial movement of spreader 14 has actuated pump 16 by the distance that releases a full drug dose. By anticipating the click, the user will know whether spreader 14 needs to be depressed further so that the user is less likely to accidentally dispense a partial drug dose. The click can be an audible sound that the user can hear and/or a tactile pulse that the user can feel. Referring to FIG. 12C for example, spring 92 can provide an upward force such that, with a sufficient difference between distance 102 and distance 108, an audible sound and tactile pulse is generated when teeth 86 impact ramp surfaces 98.

Device 10 includes a gate mechanism that can help prevent the user from purposefully or accidentally dispensing a partial drug dose. The gate mechanism has the effect of causing spreader 14 to be depressed completely when a force or pressure exceeding a threshold level is applied to spreader 14. For example, the gate mechanism engages spreader 14 to prevent spreader 14 from moving when pressure is too low, i.e., below a pressure threshold value. The pressure threshold value is an amount of pressure that will reliably actuate pump 16 completely to release the full drug dose. When the user applies more pressure to spreader 14 so as to meet or exceed the pressure threshold value, the gate mechanism disengages spreader 14 and the buildup of pressure causes spreader 14 to be depressed quickly and completely.

Referring to FIGS. 1, 8 and 13-16, spreader 14 can include first portion 110 and second portion 112. Drug passageway 24 is disposed at an interface between first portion 110 and second portion 112. Second portion 112 can be made of an elastic material so that it forms a flexible wall of drug passageway 24. First portion 110 is configured to allow the drug dose released from chamber 22 of container 12 to pass through drug passageway 24 when pump 16 is actuated by spreader 14. When pump 16 forces the drug dose into drug passageway 24, the flexible wall yields to allow the drug dose to continue through the entire drug passageway and exit from outlets 26.

First portion 110 is further configured to obstruct air flow in drug passageway 24 after the drug dose has passed through drug passageway 24. This can help prevent contamination of drug passageway 24 and minimize the volume of drug remaining in spreader 14 which is outside of the sterile environment of chamber 22 of container 12. Any quantity of the drug dose that might remain in drug passageway 24 will be squeezed out of drug passageway 24 by the flexible walls provided by first portion 110. After the drug dose has passed entirely through drug passageway 24, the flexible wall returns to its natural, collapsed state in which it presses against second portion 112 so that the entire drug passageway 24, or only a segment thereof, is compressed shut. Second portion 112 is formed of a material that is less flexible than that of first portion 110.

Second portion 112 covers first portion 110 and forms outer surface 18 of spreader 14. As indicated above, first portion 110 is more flexible than second portion 112. Alternatively, second portion 112 can be formed of a material that is more flexible than that of first portion 110, such that second portion 112 forms the flexible wall that squeezes out the drug dose from drug passageway 14 and then collapses onto first portion 110 to seal drug passageway 24. As a further alternative, first portion 110 and second portion 112 can be made of flexible materials such that both portions 110, 112 form flexible walls of drug passageway 24 which squeeze out the drug dose from drug passageway 24 and then collapse onto each other to seal drug passageway 24.

Any of the above embodiments and aspects of the invention can be modified such that spreader 14 includes any one or more of the features described above in combination with any one or more features described below in connection with FIGS. 13-16.

As shown in FIG. 13, spreader 14 includes first portion 110 and second portion 112. FIG. 13 is an exploded view to more clearly illustrate the features of spreader 14. When assembled, second portion 112 rests directly on top of first portion 110. First portion 110 includes first portion upper surface 114 and first portion lower surface 116. Second portion 112 includes second portion upper surface 118 and second portion lower surface 120. Second portion upper surface 118 is used to apply the drug onto skin. When assembled, second portion lower surface 120 is disposed on and in contact with first portion upper surface 114.

The terms "upper" and "lower" refer to the orientation of components as illustrated in the figures. It will be appreciated that the components can be inverted or oriented in various directions when in use. For example, when device 10 is inverted, an upper surface can be located below a corresponding lower surface on the same component. Thus, the terms "upper" and "lower" should not be interpreted as limiting the scope of the invention to one orientation (e.g., upright, inverted, or tilted).

Drug inlet 64 is an aperture formed through first portion lower surface 116. A segment of drug passageway 24 extends from drug inlet 64 to first portion aperture 121 formed through first portion upper surface 114. Drug outlets 26 are apertures formed through second portion upper surface 118. Other segments of drug passageway 24 extend from drug outlets 26 to apertures 122 formed through second portion lower surface 120. Although only two drug outlets 26 are illustrated, it will be appreciated that there can be only one or many more drug outlets. Pump 16 forces the drug into drug inlet 64, through the contact interface between second portion lower surface 120 and first portion upper surface 114, and out of drug outlets 26 where the drug can then be spread on the skin.

In FIG. 13, drug outlets 26 are offset from drug inlet 64. Each drug outlet 26 is separated by radial distances D from drug inlet 64. Second portion lower surface 120 covers first portion aperture 121. This configuration can prevent or reduce the possibility that actuation of pump 16 could cause the drug to stream or jet out of drug outlets 26. Second portion lower surface 120 would deflect the drug coming out of first portion aperture 121 and distribute the drug to one or more drug outlets 26.

In some aspects, contact between second portion lower surface 120 and first portion upper surface 114 can be momentarily lost when the drug is forced through. After the drug has passed through, contact between second portion lower surface 120 and first portion upper surface 114 is restored. Such contact can inhibit or prevent leaks of drug from the drug passageway of first portion 110 in the absence of positive pressure. Positive pressure refers to a positive differential in pressure between drug inlet 64 (at higher pressure) and drug outlets 26 (at lower pressure). For example, the positive differential can be such that the gauge pressure (e.g., fluid pressure of drug) at drug inlet 64 is at least two times or at least ten times the gauge pressure at drug outlets 26 (e.g., ambient air pressure). The positive differential can be produced by pump 16 when it is actuated by the user.

In FIG. 14, grooves 124 are optionally formed into first portion upper surface 114. Groves 124 provide a passageway for the drug upon dispensing. Grooves 124 extend radially outward from first portion aperture 121. Grooves 124 optionally intersect with first portion aperture 121 as illustrated. Although only three grooves 124 are illustrated, it will be appreciated that a greater or lesser number of grooves can be implemented.

FIGS. 15A and 15B are alternative plan views that show second portion 112 superimposed over first portion 110 as viewed along arrow 21 in FIG. 13. In FIG. 15A, drug outlets 26 are offset from grooves 124. Drug outlets 26 and apertures 122 (FIG. 13) are not located directly above grooves 124. The configuration of FIG. 15A may reduce the possibility of streaming and/or may inhibit leaking of drug from the drug passageway of first portion 110 in the absence of positive pressure. In FIG. 15B, drug outlets 26 are aligned with grooves 124. Drug outlets 26 and apertures 122 (FIG. 13) are located directly above grooves 124. The configuration of FIG. 15B can increase the speed at which the drug is distributed over large areas of second portion upper surface 118 when pump 16 is actuated.

In some aspects, second portion 112 is optionally a membrane made of an elastic polymer material. Second portion upper surface 118 and second portion lower surface 120 are on opposite sides of the membrane. The membrane is flexible and conforms to the shape of first portion 110. Peripheral edges 126 (FIG. 13) of the membrane (or other areas of the membrane) can be affixed onto first portion 110 so that second portion lower surface 120 naturally presses against first portion upper surface 114. With positive pressure, such as when pump 16 is actuated, the drug pushes against second portion lower surface 120 of the membrane, which causes the membrane to flex to allow passage of the drug. In the absence of positive pressure, elasticity of the membrane causes second portion lower surface 120 to press once again against first portion upper surface 114. This configuration can inhibit or prevent leaks of drug from the drug passageway of first portion 110 in the absence of positive pressure.

In some aspects, one or more annular drug channels 38 are formed into second portion upper surface 118, such as shown in FIGS. 2, 3, 4, and 16-19. Drug channels 38 can retain an amount of drug discharged from drug outlets 26 and thereby reduce the possibility of the drug dripping down the sides of spreader 14 before it can be spread onto the skin of the user. Optionally, there are no drug outlets 26 at outer drug channel 38B as illustrated in FIG. 16. In FIG. 16, drug outlets 26 are located within inner drug channel 38A, and outer drug channel 38B can capture a quantity of drug that may overflow from inner drug channel 38A.

In some aspects, first portion 110 and second portion 112 of spreader 14 are made of a rigid material, such as acrylonitrile butadiene styrene (ABS) or other polymer which is compatible with the drug.

Figure 17:
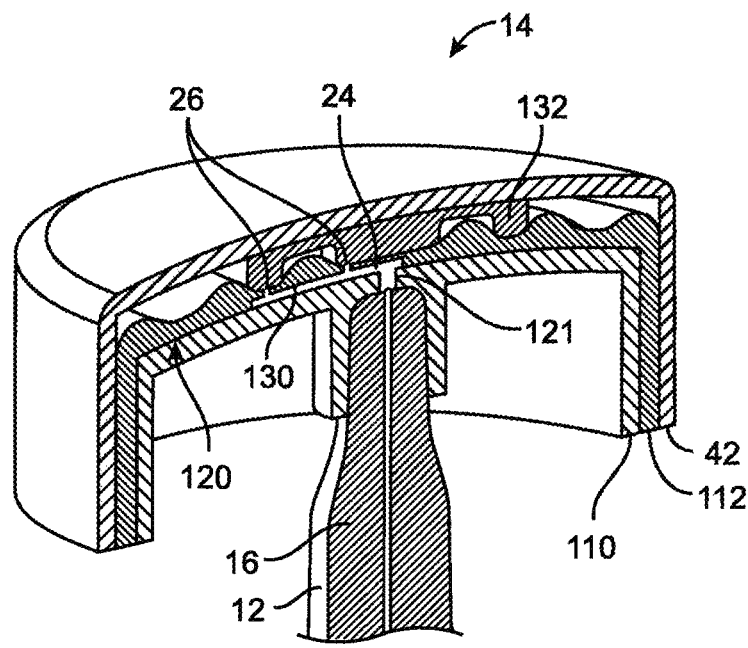
FIGS. 17-20 are perspective section views showing variously exemplary spreaders for topical application of a drug.

In FIG. 17, first portion 110 and second portion 112 of spreader 14 are made of a rigid material, such as ABS or other material. Grooves 130 are formed into second portion lower surface 120. Each groove 130 forms a segment of drug passageway 24 between first portion aperture 121 and second portion drug outlets 26. Although only one groove is visible, it should be understood that any number of grooves 130 may be formed into second portion lower surface 120 depending upon the number and location of drug outlets 26. One end of each groove 130 is adjacent to and is in fluid communication with first portion aperture 121. The opposite end of groove 130 is adjacent to and in fluid communication with drug outlet 26.

Groove 130 does not collapse or form a seal since first portion 110 and second portion 112 are both rigid. Drug passageway 24 can be sealed by gasket 132 attached to cover 42. Portions of gasket 132 press against areas of second portion 112 where drug outlets 26 are located. Gasket 132 can prevent amounts of drug within passageway 24 from evaporating, which allows passageway 24 to remain filled with drug. When passageway 24 remains filled with drug, delivery of drug out of second portion drug outlets 26 will occur immediately upon actuation of pump 16. Gasket 132 can be made of a resilient material conforms to the surface contours of first portion 110.

Figure 18:
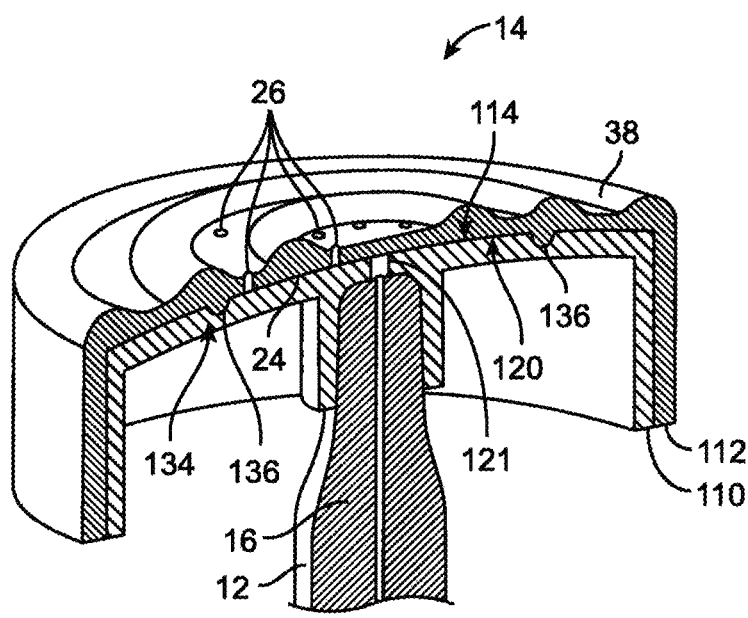

In FIG. 18, first portion 110 is made of a rigid material, such as ABS or other material. Second portion 112 is made of a flexible material, such as silicone, thermoplastic elastomer (TPE), or other material. The interface between first portion 110 and second portion 112 forms drug passageway 24 capable of self-collapsing or self-sealing. Drug passageway 24 is not formed by any groove formed into first portion 110 or second portion 112. When drug passageway 24 is in its sealed state, as illustrated in FIG. 18, second portion lower surface 120 is in contact with first portion supper surface 114. In the sealed state, the interface is the area of contact between first portion 110 and second portion 112. Flexibility of second portion lower surface 120 allows it to conform to the contour of first portion supper surface 114. When pump 16 is actuated, the drug is forced into the interface. The hydraulic pressure causes second portion 112 to flex or stretch slightly, allowing it to separate from first portion 110. At this time, the interface or drug passageway 24 is in an open state, which allows the drug to travel to second portion drug outlets 26. Resistance from first portion 110 urges the drug out of second portion drug outlets 26. Thereafter, drug passageway 24 returns to its collapsed state or sealed state.

Portions of second portion lower surface 120 can be secured, such as by ultrasonic welding or adhesive, to first portion upper surface 114. This is done to prevent the drug from traveling to areas of spreader 14 which do not have drug outlets 26. For example, securement 134 can form a ring which surrounds drug outlets 26. Securement 134 can be any one or a combination of a weld, adhesive, and structural element which secure portions of second portion lower surface 120 to first portion upper surface 114. An exemplary structural element is annular seal 136 that includes an annular protrusion on second portion lower surface 120 which fits into and is affixed to an annular depression in first portion upper surface 114.

In FIG. 18, second portion 112 functions as a valve member that allows drug passageway 24 to open and close. Spreader 14 can also employ a valve member that is distinct from second portion 112, as described below.

Figure 19:
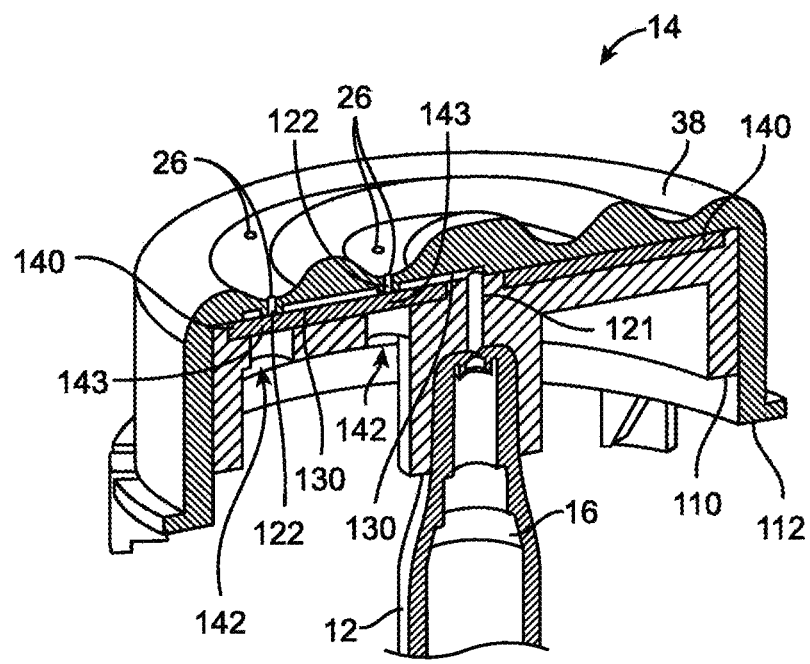

In FIG. 19, first portion 110 and second portion 112 of spreader 14 are made of a rigid material, such as ABS or other material. Grooves 130 are formed into second portion lower surface 120. Grooves 130 function as described above for FIG. 17. Grooves 130 lead to apertures 122 formed into second portion lower surface 120. Each aperture 122 is in fluid communication with a drug outlet 26. Edges of apertures 122 protrude from second portion upper surface 120. The aperture edges are pressed into contact with valve member 140 disposed between first portion supper surface 114 and second portion lower surface 120. Valve member 140 is made of a material that is less stiff than first portion 110 and second portion 112, and optionally can be made of elastic material, such as silicone, TPE, or other material.

When pump 16 is actuated, the drug is forced into grooves 130. During pump actuation, hydraulic pressure in the grooves 130 increases until the pressure causes valve member 140 to flex or stretch slightly, allowing it to separate from the edges of second portion apertures 122. When this happens, the drug is able to escape out of second portion drug outlets 26, which reduces the hydraulic pressure and allows the valve member 140 to once again press against and seal the edges of second portion apertures 122. Movable portion 143 of valve portion 140 flexes or bends away from second portion apertures 122. Movable portion 143 located directly above and is aligned with depression 142.

Depression 142 is formed into areas of first portion upper surface 114 directly below the edges of apertures 122 in second portion lower surface 120. Depression 142, which can be a through hole as illustrated or a blind hole, facilitates flexing or stretching of valve member 140. Depression 142 forms an empty space into which valve member 140 can move to allow portion 143 valve member 140 to move out of contact from the edges of second portion apertures 122 when there is sufficient hydraulic pressure within groove 130.

In FIG. 19, the drug is supplied to two second portion drug outlets 26 by a single groove 130. The spreader can be configured so that the drug is supplied to each second portion drug outlet 26 by its own groove 130 as described below.

Figure 20:
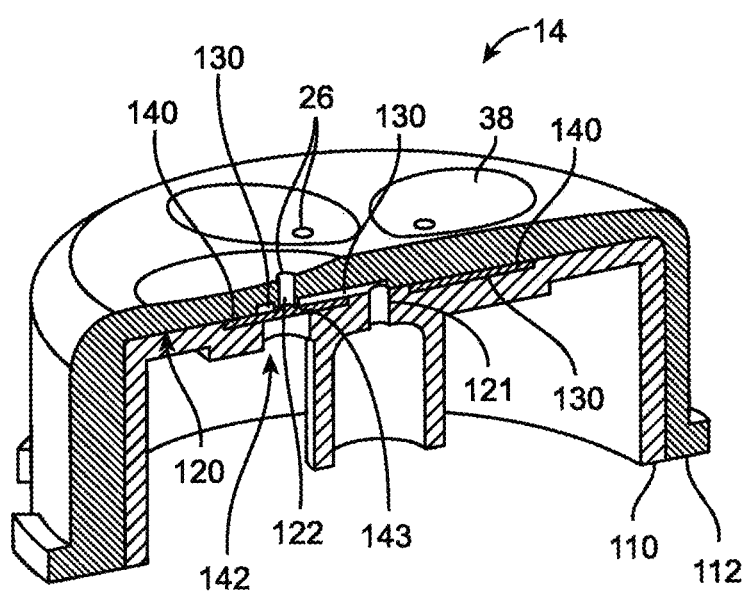
Figure 21:
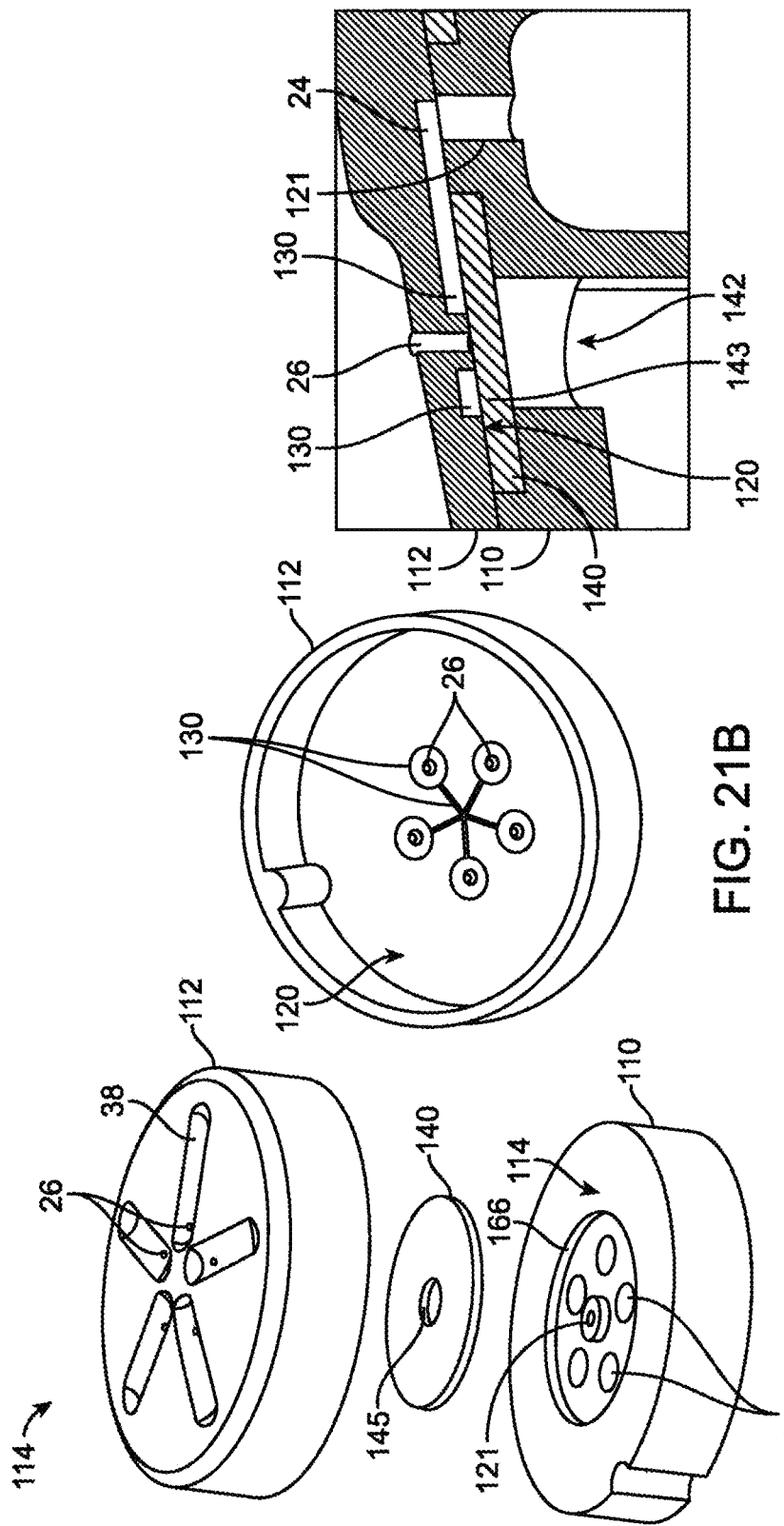
FIG. 21A is an exploded view of exemplary components for a spreader for topical application of a drug.
FIG. 21B is a perspective view showing a second portion of the spreader of FIG. 21A.
FIG. 21C is perspective section view partially showing the spreader of FIG. 21A when assembled.

Spreader 14 of FIG. 20 is configured like that of FIG. 19 except each groove 130 supplies the drug to only a single second portion drug outlet 26, and except for: the arrangement of drug channels 38 on the exterior of second portion 112, and the arrangement of depressions 142 in first portion 110. As shown in FIG. 21A, valve member 140 is a circular disc with a central opening 145 which receives the drug from first portion aperture 121. Central opening 145 is always open and is aligned with or concentric with first portion aperture 121. Valve member 140 fits into pocket 166 formed into first portion upper surface 114. As shown in FIG. 21B, grooves 130 are formed into second portion lower surface 120. Grooves 130 extend radially outward from a central point directly above first portion aperture 121.

In FIGS. 19, 20 and 21A-21C, resiliency of valve member 140 allows it to move away from and into contact with the edges of second portion apertures 122. A valve spring can be used with the valve member as described below.

Figure 22:
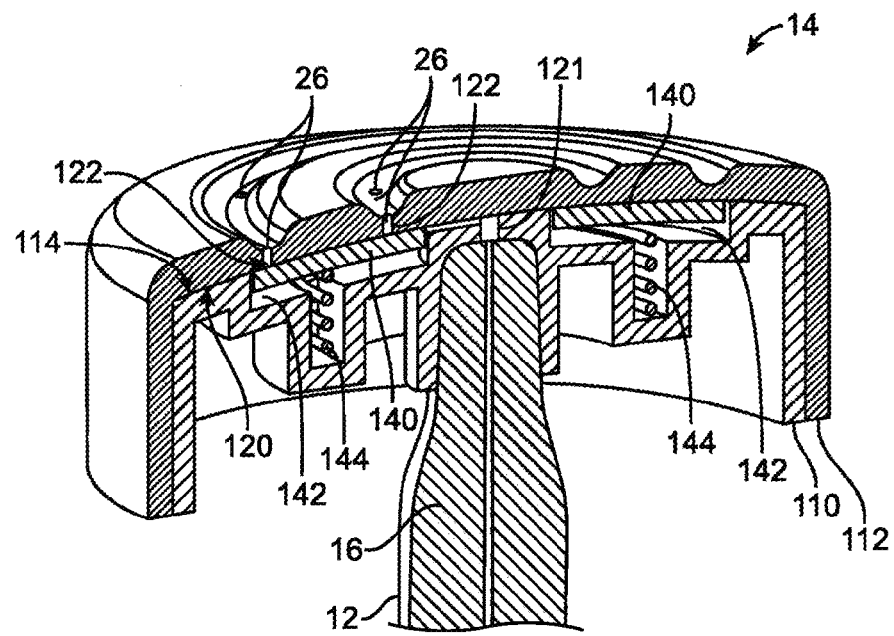

In FIG. 22, first portion 110 and second portion 112 of spreader 14 are made of a rigid material, such as ABS or other material. Edges of second portion apertures 122 are pressed into contact with valve member 140 disposed between first portion supper surface 114 and second portion lower surface 120. Valve member 140 is confined within depression 142 formed into first portion upper surface 114. Valve spring 144 is coupled to valve member 140 and applies a spring force that urges valve member 140 to press against the edges of second portion aperture 122. Valve spring 144 can be a helical spring, as illustrated, or a leaf spring or other type of spring.

When pump 16 is actuated, the drug is forced into the interface between second portion 112 and valve member 140. During pump actuation, hydraulic pressure at the interface increases until the pressure overcomes the spring force of valve spring 144. This causes valve spring 144 to yield, which allows valve member 140 to move further into depression 142 and thereby separate from the edges of second portion apertures 122. When this happens, the drug is able to escape out of second portion drug outlets 26, which reduces the hydraulic pressure and allows the valve member 140 to once again press against and seal the edges of second portion apertures 122.

Figure 23:
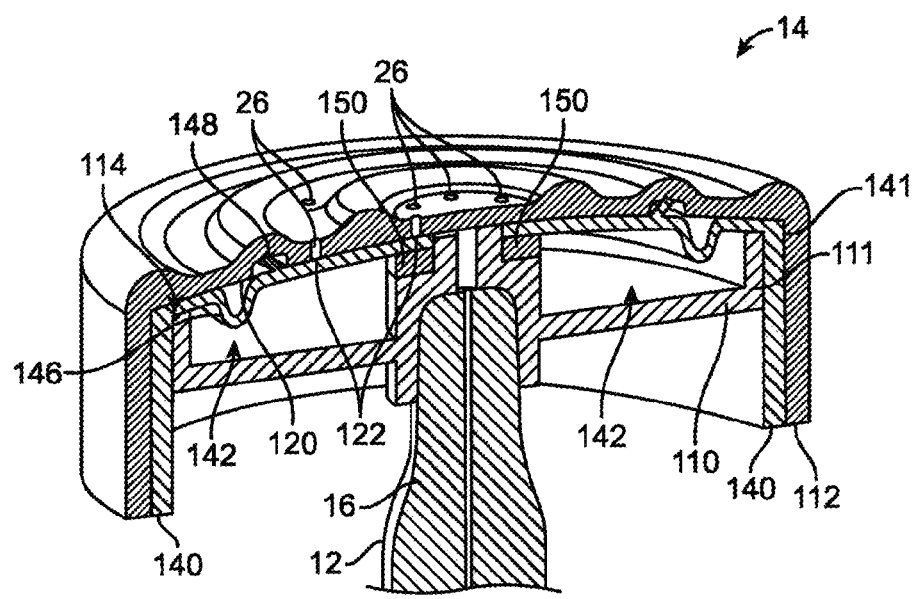

In FIG. 23, first portion 110, second portion 112, and valve member 140 are made of a rigid material, such as ABS or other material. Edges of second portion apertures 122 are pressed into contact with valve member 140 disposed between first portion supper surface 114 and second portion lower surface 120. Cylindrical sides 141 of valve member 140 can be secured to second portion 112 by ultrasonic welding, an adhesive, or other securement. Valve member 140 is supported by periphery 111 of first portion 110. Valve member 140 is cantilevered above depression 142 formed into first portion upper surface 114. Valve member 140 has a cross-sectional profile and thickness that allows it to bend into depression 142 due to hydraulic pressure when pump 16 is actuated. For example, the cross-sectional profile can include bend 146 that is configured to yield and thereby allow other areas of valve member 140 to separate from the edges of second portion apertures 122 when the drug is forced between second portion 112 and valve member 140 as a result of pump actuation.

Annular lip seal 148 protrudes from the upper surface of valve member 140 and is confined within an annular depression in second portion lower surface 120. Annular lip seal 148 encircles second portion drug outlets 26 and prevents or inhibits the drug from traveling to areas of spreader 14 that do not have drug outlets 26. Optionally, gasket 150 is disposed below the interface between valve member 140 and first portion 110 to prevent or inhibit leakage of the drug during pump actuation.

In FIGS. 19-23, the drug travels above valve member 140 and within a space between valve member 140 and second portion 112. Spreader 14 can be configured such that the drug travels below the valve member as described below.

Figure 24A:
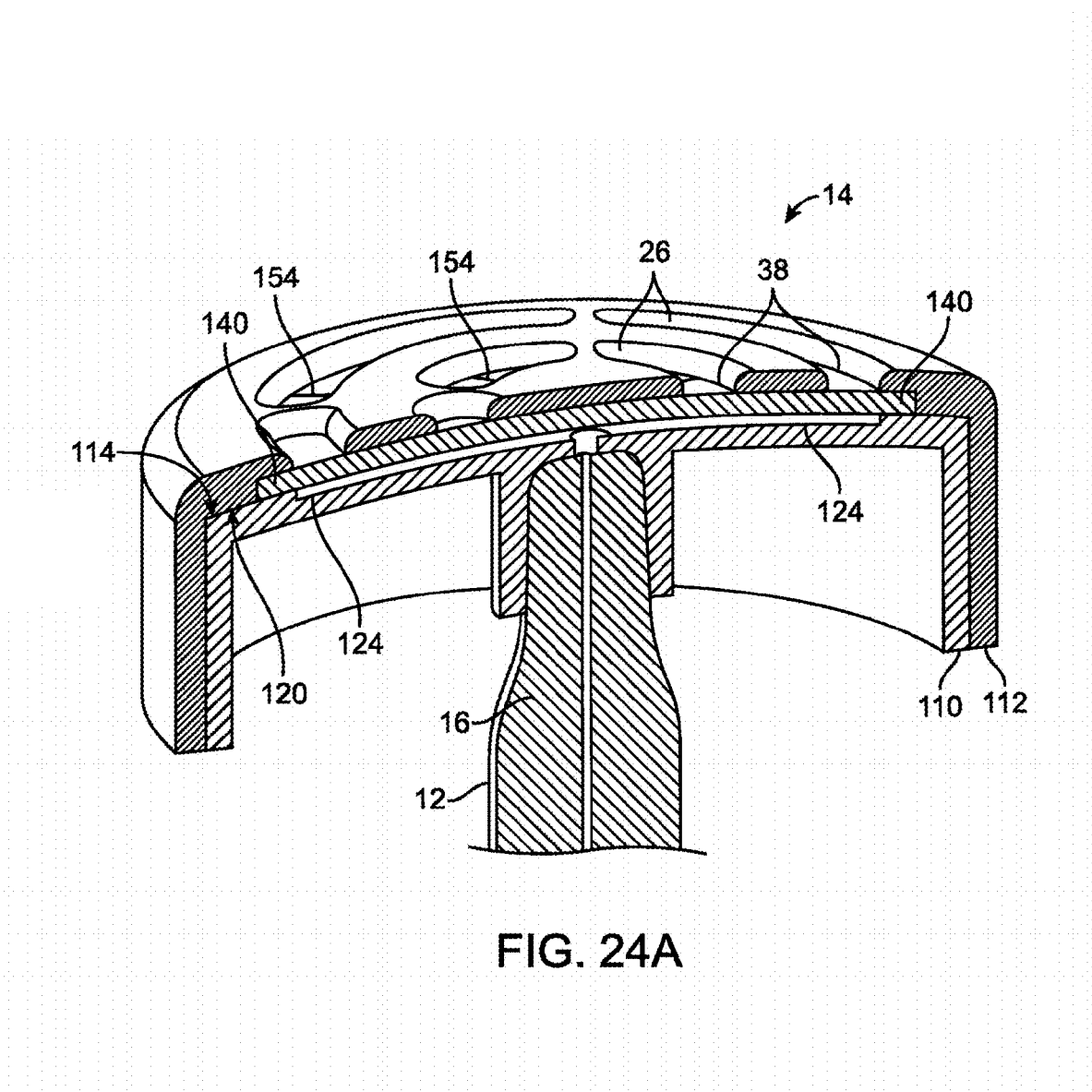
Figure 24B:
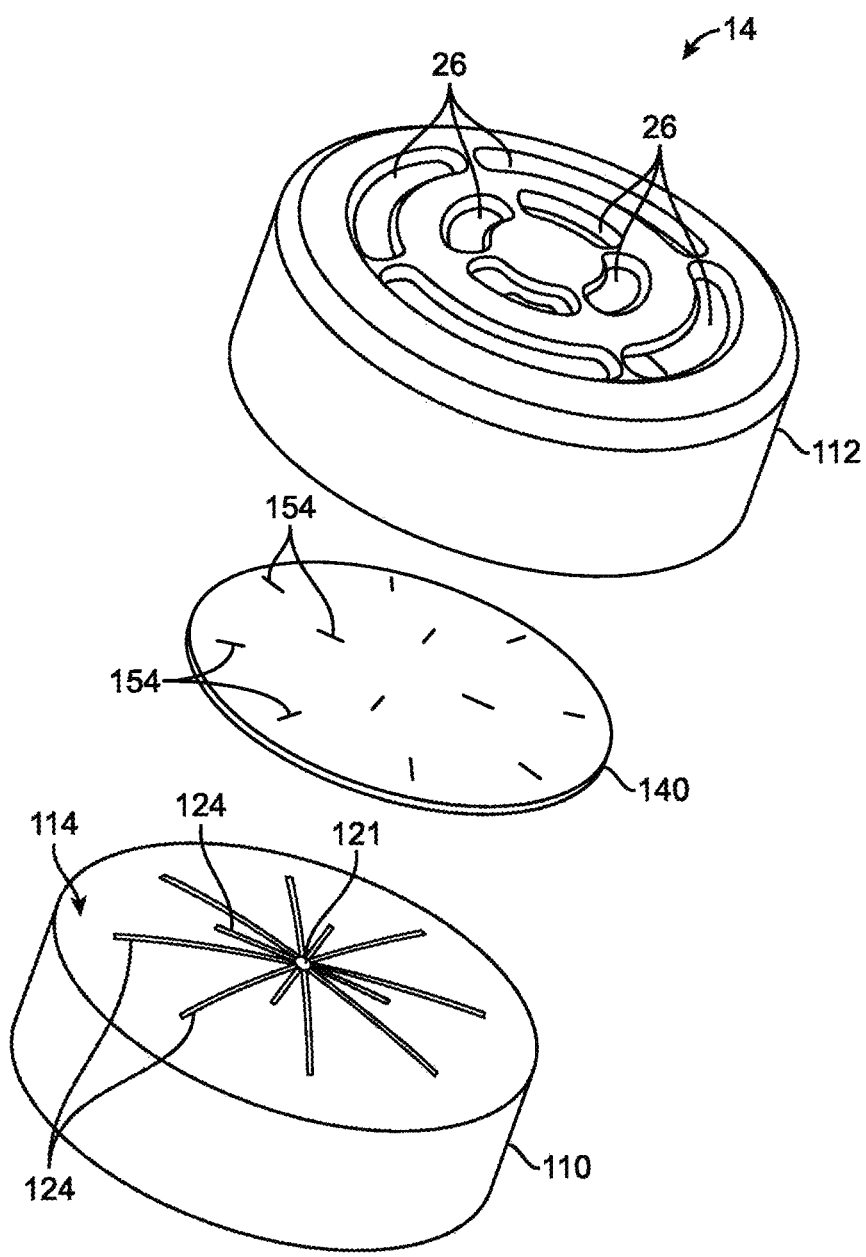
FIG. 24B is an exploded view of exemplary components for the spreader of FIG. 24A.

In FIGS. 24A and 24B, first portion 110 and second portion 112 are made of a rigid material, such as ABS or other material. Valve member 140 is a round disc made of a material that is less stiff than first portion 110 and second portion 112, and optionally can be made of elastic material, such as silicone, TPE, or other material. Grooves 124 are formed into first portion upper surface 114. A plurality of slits 154 are formed through the valve member 140. Slits 154 are located directly below second portion drug outlets 26. Slits 154 are normally closed. Flexibility of valve member 140 allows slits 154 to open when pump 16 is actuated. During pump actuation, the drug is forced into grooves 124 below valve member 140. Hydraulic pressure in the grooves 124 increases until the pressure causes the slits 154 to open. Optionally, second portion drug outlets 26 are enlarged, as illustrated, so that areas of valve member 140 immediately adjacent to slits 154 can flex upward into the empty space within second portion drug outlets 26 in response to hydraulic pressure and enable slits 154 to open. Enlarged second portion drug outlets 26 may also function as cups, like drug channels 38 of FIGS. 3 and 4, that temporarily contain the drug while the user slides spreader 14 across the skin.

Figure 25C:
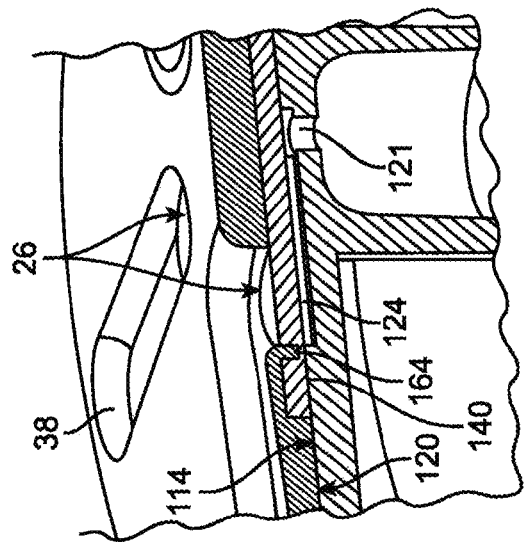
FIG. 25C is perspective section view partially showing the spreader of FIG. 25A when assembled.
Figure 25B:
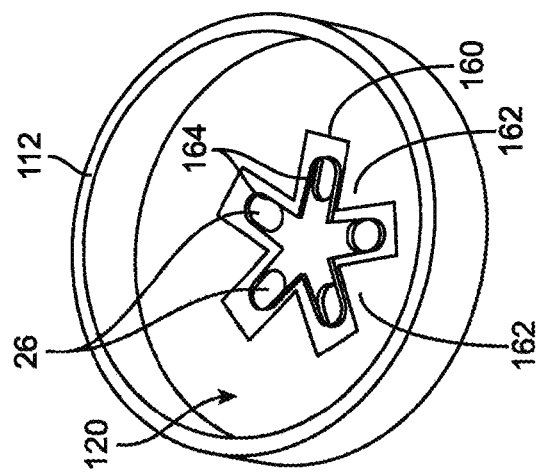
FIG. 25B is a perspective view showing a second portion of the spreader of FIG. 25A.
Figure 25A:
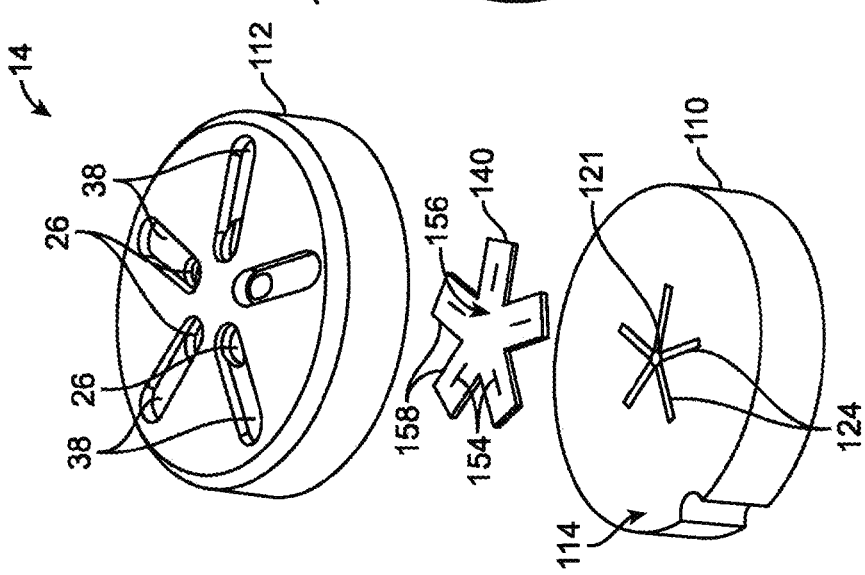
FIG. 25A is an exploded view of exemplary components for a spreader for topical application of a drug.

In FIGS. 25A-25C, first portion 110 and second portion 112 are made of a rigid material, such as ABS or other material. Valve member is made of a material that is less stiff than first portion 110 and second portion 112, and optionally can be made of elastic material, such as silicone, TPE, or other material. The construction of spreader 14 in FIGS.

25A-25C is like that of FIGS. 24A and 24B except valve member 140 is not a round disc and drug channels 38 are formed on the exterior surface of second portion 112. Valve member 140 has slits 154 that flex from a sealed state to an open state in response to an increase in hydraulic pressure in grooves 124 during pump actuation.

To enhance drug delivery efficiency, valve member 140 is configured to prevent or inhibit the drug from moving to areas within spreader 14 which are distant from slits 154. Valve member 140 includes center portion 156 and a plurality of arms 158 that project radially outward from the center portion. Center portion 156 has no slit. Center portion 156 is located over first portion aperture 121. Slits 154 are formed through arms 158. Grooves 124 extend radially outward from first portion aperture 121 toward slits 154. Valve member 140 fits within pocket 160 formed into second portion lower surface 120. Pocket 160 is a depression having has a shape that matches the shape of valve member 140. Portions 162 of second portion 112 which surround pocket 160 are disposed within the gaps between arms 158 of valve member 140. Portions 162 of second portion 112 remain in contact with first portion 110, which can help to limit the drug from traveling beyond the outer boundaries of valve member 140.

Second portion 112 of spreader 14 is also configured to enhance drug delivery efficiency. As shown in FIG. 25B, second portion drug outlets 26 are formed within the depression of pocket 160. Rib 164 (also referred to as a pinch rim) protrudes from the depression. Rib 164 surrounds all second portion drug outlets 26. Rib 164 pinches or presses into valve member 140. Rib 164 functions like a fence that further helps to limit the drug from traveling beyond the outer boundaries of valve member 140.

In FIGS. 24A, 24B and 25A-25C, there is at least one slit 154 that supplies the drug to each second portion drug outlet 26. Spreader 14 can be configured such that a single slit in the valve member can supply a plurality of second portion drug outlets, as described below. A single slit can avoid problems associated with multiple slits in which one slit opens before other slits, which results in reduction of hydraulic pressure and prevents the drug from being released from the other slits.

Figure 26C:
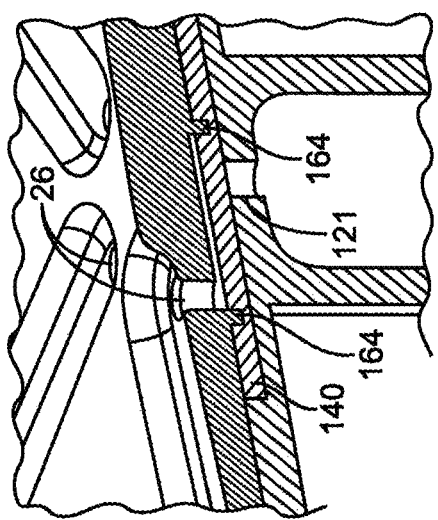
FIG. 26C is perspective section views partially showing the spreader of FIG. 26A when assembled.
Figure 26B:
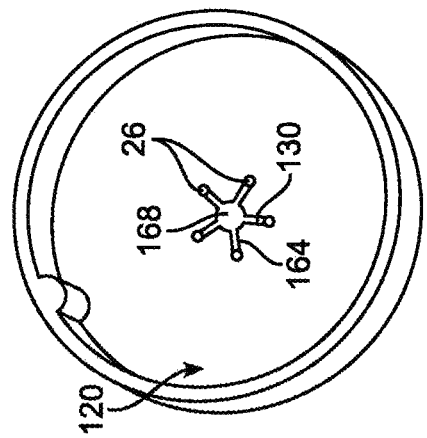
FIG. 26B is a perspective view showing a second portion of the spreader of FIG. 26A.
Figure 26A:
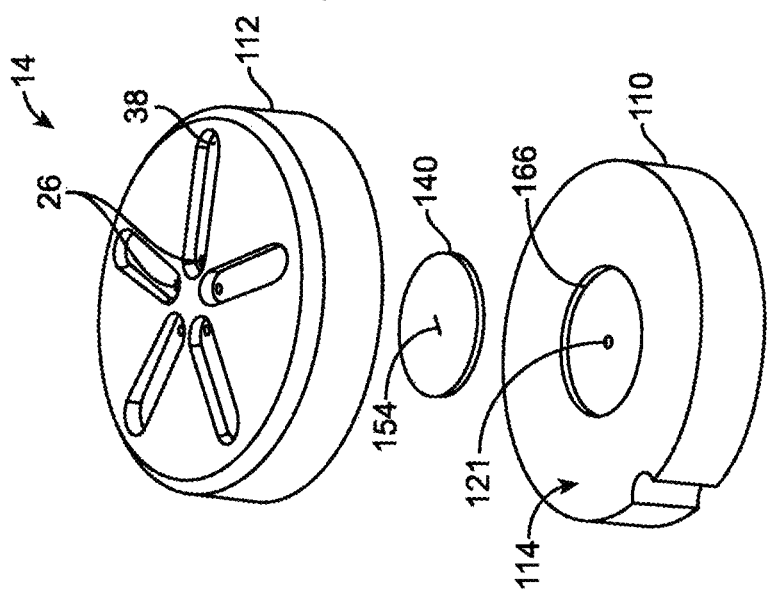
FIG. 26A is an exploded view of exemplary components for a spreader for topical application of a drug.

In FIGS. 26A-26C, first portion 110 and second portion 112 are made of a rigid material, such as ABS or other material. Valve member 140 is a round disc made of a material that is less stiff than first portion 110 and second portion 112, and optionally can be made of elastic material, such as silicone, TPE, or other material. Valve member 140 has only a single slit 154. Single slit 154 supplies the drug to a plurality of drug outlets 26.

Valve member 140 is sandwiched between first portion 110 and second portion 112. Valve member 140 is retained within pocket 166 formed in first portion upper surface 114. Slit 154 is located directly above first portion aperture 121. Slit 154 flexes from a sealed state to an open state in response to an increase in hydraulic pressure at first portion aperture 121 during pump actuation. None of the drug outlets 26 are located directly above slit 154 to inhibit or prevent the drug from jetting out in a stream from spreader 14. Grooves 130 and central depression 168 are formed into second portion lower surface 120. Grooves 130 extend radially outward from central depression 168 to drug outlets 26. During pump actuation, the drug flows through slit 154 and travels through grooves 130 to drug outlets 26. Central depression 168 provides a space for valve member 140 to move upward and to flex so that slit 154 may open in response to hydraulic pressure.

To enhance drug delivery efficiency, second portion 112 is configured to prevent or inhibit the drug from moving to areas within spreader 14 which are distant from drug outlets 26. As shown in FIGS. 26B and 26C, rib 164 (also referred to as a pinch rim) protrudes from second portion lower surface 120. Rib 164 is disposed at the perimeter of all grooves 130 and central depression 168. Rib 164 pinches or presses into valve member 140. Rib 164 functions like a fence that helps to limit the drug from traveling outside of grooves 130.

In FIGS. 24A, 25A, and 26A, valve member 140 has one or more slits 154 that open and close in response to hydraulic pressure. As discussed below, the valve member can have one or more openings which remain open at all times.

Figure 27:
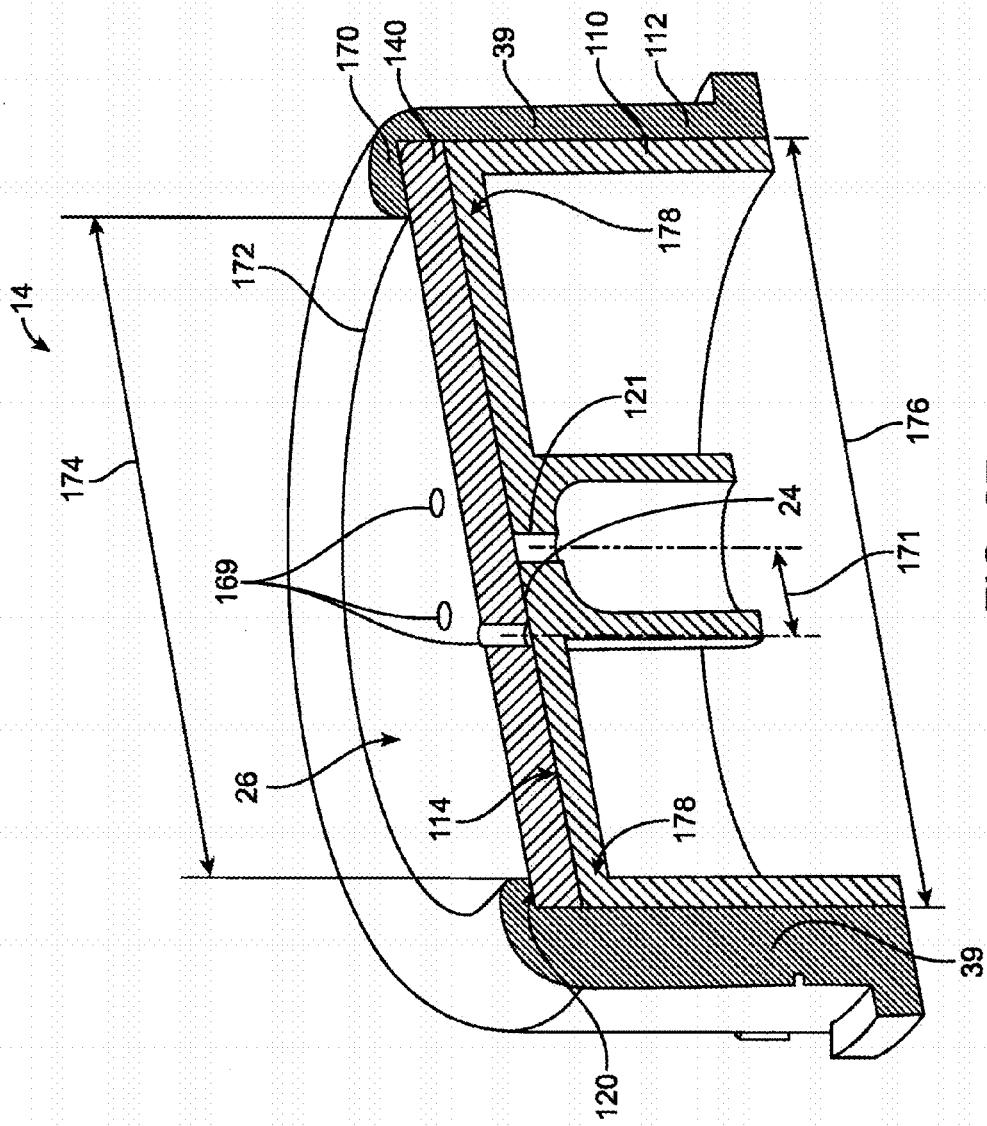
FIG. 27 is a perspective section view showing an exemplary spreader for topical application of a drug.
Figure 28D:
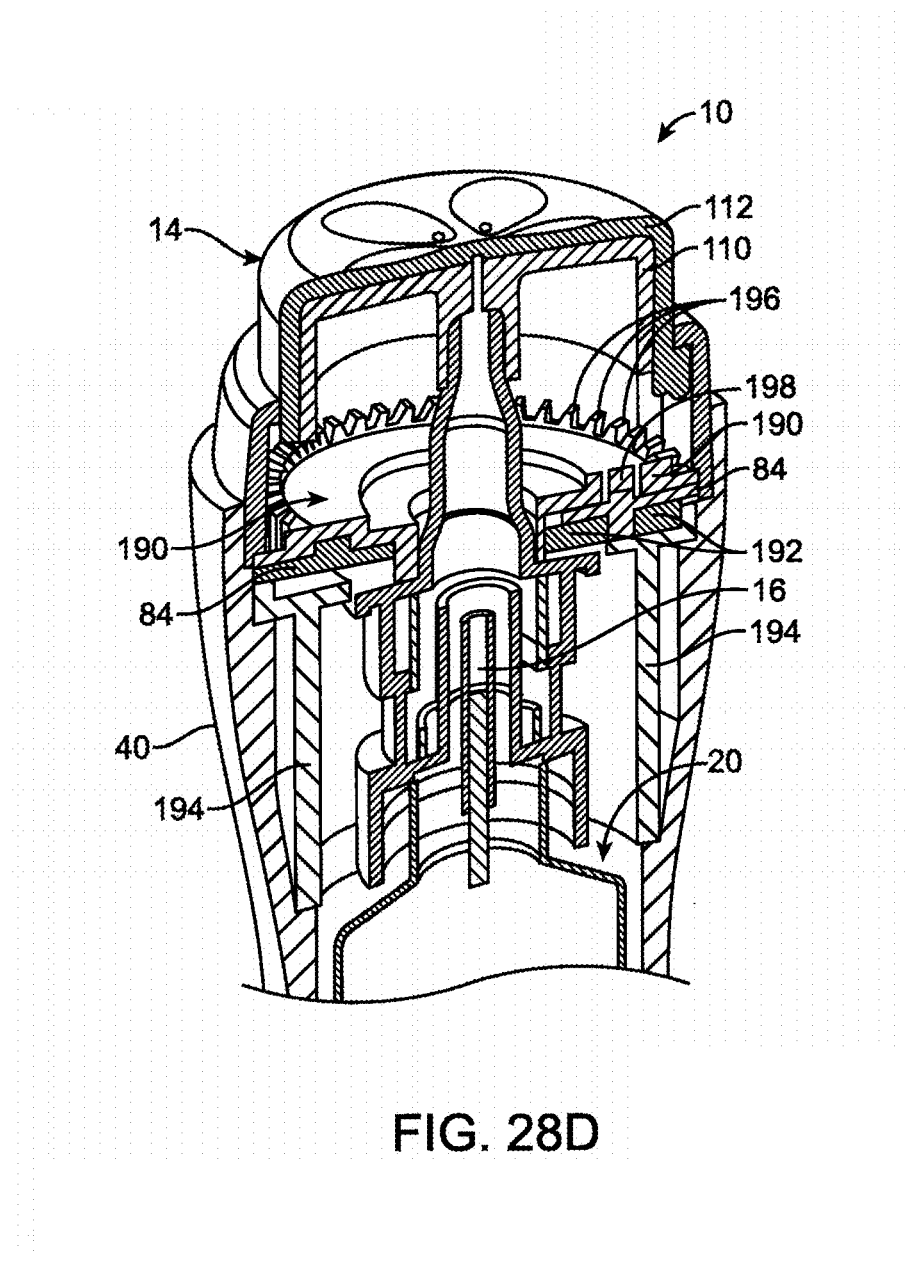
FIG. 28D is a perspective section view showing the rotatable parts of the lock in the device of FIG. 28A.

In FIG. 27, first portion 110 and second portion 112 of spreader 14 are made of a rigid material, such as ABS or other material. Valve member 140 is made of a material that is less stiff than first portion 110 and second portion 112, and optionally can be made of elastic material, such as silicone, TPE, or other material. Valve member 140 functions like the second portion 112 of FIG. 18. A plurality of valve member through holes 169 are formed through valve member 140. Valve member through holes 169 remain open at all times. None of the valve member through holes are located directly above first portion aperture 121 of first portion 110, which inhibits or prevents the drug from jetting out in a stream from spreader 14 during pump actuation. Each through hole 169 is radially offset from first portion aperture 121 by radial distance 171.

Top end 170 of second portion 112 extends radially inward. Inner edges 172 of top end 170 define edges of a single second portion drug outlet 26. Second portion drug outlet 26 has diameter 174 that is from 0.7 to 0.9 times inner diameter 176 inner diameter of cylindrical sides 39 of second portion 112. Valve member 140 is secured between top end 170 of second portion 112 and first portion upper surface 114. Optionally, valve member 140 secured (such as by ultrasonic welding, adhesive, or other means) to any one or more of top end 170 of second portion 112, cylindrical sides 39 of second portion 112, and perimeter 178 of first portion 110. When valve member 140 is in a closed position, valve member 140 is in contact with areas of first portion upper surface 114. Flexibility of valve member 140 allows it to conform to the contour of first portion upper surface 114.

When pump 16 is actuated, the drug is forced into the interface between valve member 140 first portion upper surface 114. Hydraulic pressure at first portion aperture 121 increases until the pressure causes valve member 140 to flex or stretch slightly in an upward direction, allowing it to separate from first portion upper surface 114. The enlarged drug outlet 26 formed in second portion 112 provides an empty space above valve member 140 to allow valve member 140 flex or stretch slightly in an upward direction in response to the hydraulic pressure. When this happens, the drug is able to flow out of first portion aperture 121 and into the space between valve member 140 and first portion upper surface 114. At this time, the interface or drug passageway 24 is in an open state, which allows the drug to travel to valve member through holes 169. Resistance from valve member 140 urges the drug out of through holes 169 and drug outlets 26. Thereafter, drug passageway 24 returns to its collapsed state or sealed state. Top end 170 of second portion 112 forms a rim that may also function like a cup that temporarily contains the drug while the user slides spreader 14 across the skin.

As discussed above, various aspects of the invention optionally include one or more drug channels 38 formed into the upper surface of second portion 112. Any of the second portions 112 described herein can be modified to include one or more curved drug channels 38 which form concentric circles (e.g., FIGS. 8 and 18), one or more drug channels 38 which are curved but do not form closed circles (e.g., FIG. 24A), one or more drug channels 38 which are linear and extend radially outward from a drug aperture (e.g., FIGS. 21A and 25B), and one or more drug channels 38 which are oval in shape having one end with a first radius of curvature near a drug opening 26 and an opposite end having a second radius of curvature greater than the first radius of curvature (e.g., FIG. 20). Drug channels 38 can have other patterns. Drug channels 38 can be a plurality of elongate channels formed into the upper surface of second portion 112, and the channels can intersect or cross each other to form a grid pattern on the upper surface of second portion 112. Drug channels 38 can be a plurality of depressions formed into the upper surface of second portion 112, and each channel is separated from adjacent depressions so that the plurality of channels forms a pattern of dots on the upper surface of second portion 112. The drug channels 38 may include any one or a combination of the configurations described above.

Although spreader 14 has been described above in combination with pump 16 and container 12, it will be appreciated that spreader 14 can be used to dispense drugs from other types of pumps and/or drug containers.

Any of the above aspects of the invention can be modified such that device 10 has no lock and there is no numerical limit on the total number of times pump 16 can be actuated.

Any of the above designs for spreader 14 can be combined with any of the designs for lock 50 described above, such as lock 50 described in association with FIGS. 6-8 and 21A-21C. In FIG. 8, first ring 82 of lock 50 functions as a dose counter part. The dose counter part has a portion that is visible through aperture 44 in case 40 to indicate the number of drug doses which have been delivered by device 10 or the number of drug doses remaining in device 10.

Any of the above designs for spreader 14 can be combined with any of the designs for lock 50 described below.

In FIGS. 28A-28D, device 10 has lock 50 that includes three rotatable parts: ratcheting part 190, intermediate gear 192, and dose counter part 194. Intermediate gear operatively couples ratcheting part 190 to dose counter part 194. Ratcheting part 190 is contacted and rotated by spreader 14. Intermediate gear 192 is contacted and rotated by ratcheting part 190. Dose counter part 194 is contacted and rotated by intermediate gear 192.

The bottom edge of spreader 14 includes a plurality of angled spreader teeth 195. When angled teeth 195 move into lock 50, lock 50 advances one step toward its locked state. Lock 50 is configured to advance by a total number of steps that corresponds to the total number of drug doses which device 10 is designed to deliver. The total number of steps establishes the numerical limit, previously described above, at which pump 16 can no longer be actuated by spreader 14.

Ratcheting part 190 includes angled teeth 196 and is constrained from moving axially relative to case 40. Pump 16 is actuated with downward movement of spreader 14 into case 40 in an axial direction parallel to central axis 70. When spreader 14 is pushed down by the user to actuate pump 16, angled spreader teeth 195 engage angled teeth 196 of ratcheting part 190 and pushes teeth 196 sideways such that ratcheting part 190 rotates about central axis 70. Ratcheting part 190 includes pawl 198 that engages teeth on fixed ratchet member 84 and prevents ratcheting part 190 from rotating backwards.

Ratcheting part 190 includes gear teeth 200 (FIGS. 28A and 28B) which are located closer to central axis 70 than angled teeth 196. Intermediate gear 192 includes gear teeth 202 that engage gear teeth 200, such that rotation of ratcheting part 190 causes intermediate gear 192 to rotate about axis 204 which is parallel to and offset from central axis 70. Dose counter part 194 includes gear teeth 206 that engage gear teeth 202, such that rotation of intermediate gear 192 causes dose counter part 194 to rotate about central axis 70.

Portion 208 of dose counter part 194 is visible through aperture 44 in case 40. Portion 208 is cylindrical. In FIG. 28C, portion 208 is illustrated schematically in a flattened state. Visual indicator 46 is disposed on portion 208. As dose counter part 194 rotates, visual indicator 46 shifts position so that a different area of visual indicator 46 becomes visible in aperture 44. Visual indicator 46 can be as previously described above.

In FIG. 28C, visual indicator 46 includes a graphical pattern, which may include changes in color, to indicate whether lock 50 is at or near the numerical limit, previously described above, at which pump 16 can no longer be actuated by spreader 14.

As shown in FIG. 28A, case 40 may include movable door 210 that can allow container 12 to be removed when empty and replaced with another container 12.

Figures 29A, 29B:
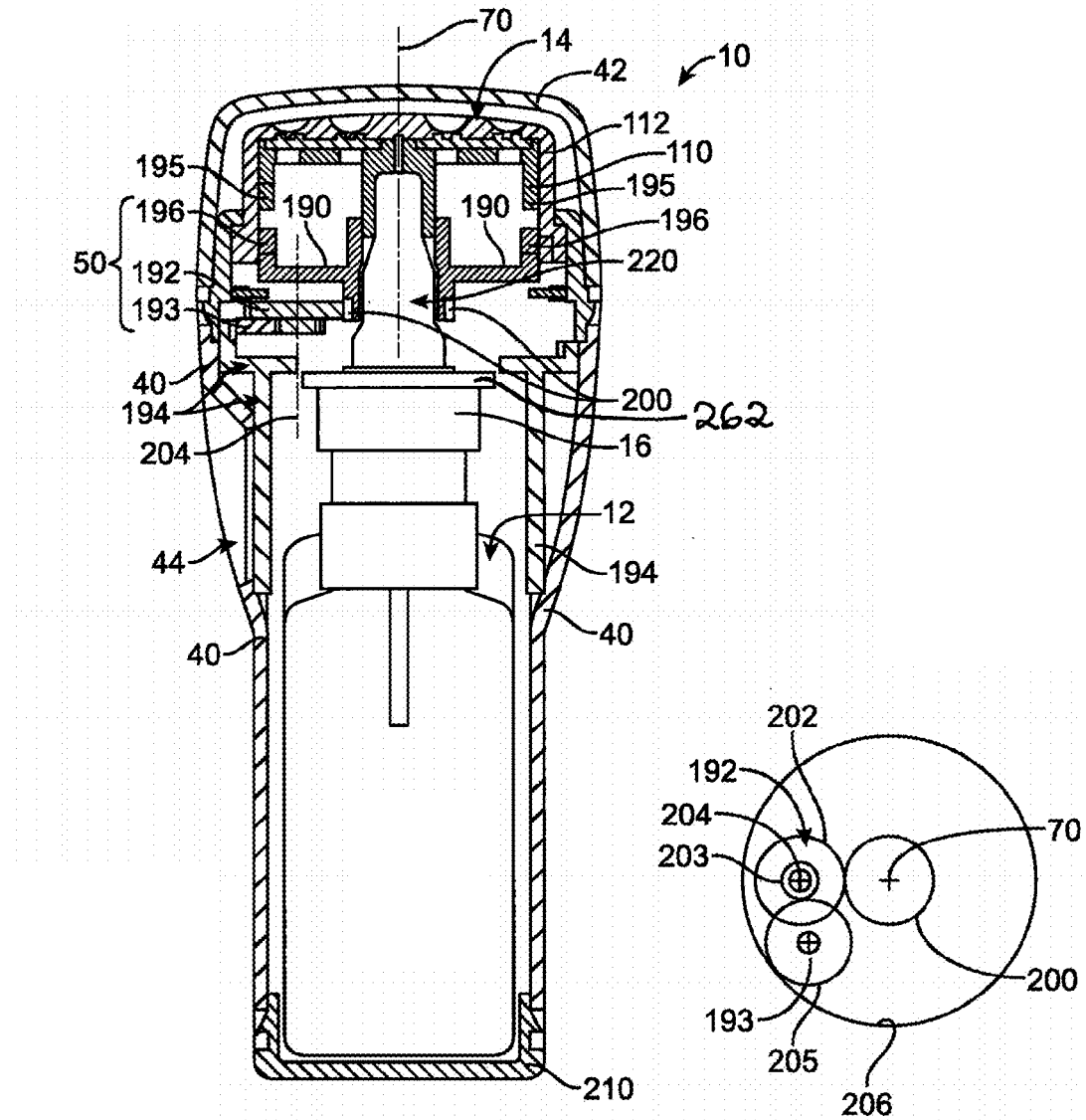
FIG. 29A is a section view showing an exemplary device for dispensing a drug.
FIG. 29B is a schematic view showing relationships between rotatable parts of a lock in the device of FIG. 29A.

In FIGS. 29A-29B, device 10 includes lock 50 that provides the same function as described for FIG. 28A. A difference is that lock 50 of FIGS. 29A-29B includes two intermediate gears. Lock 50 includes four rotatable parts: ratcheting part 190, first intermediate gear 192, second intermediate gear 193, and dose counter part 194. Ratcheting part 190 is operatively coupled to dose counter part 194 by first intermediate gear 192 and second intermediate gear 193.

Spreader 14 includes a plurality of angled spreader teeth 195. When angled teeth 195 move into lock 50, lock 50 advances one step toward its locked state. Lock 50 is configured to advance by a total number of steps that corresponds to the total number of drug doses which device 10 is designed to deliver. The total number of steps establishes the numerical limit, previously described above, at which pump 16 can no longer be actuated by spreader 14.

Ratcheting part 190 includes angled teeth 196 and is constrained from moving axially relative to case 40. When spreader 14 is pushed down by the user to actuate pump 16, angled spreader teeth 195 engage angled teeth 196 of ratcheting part 190 and pushes teeth 196 sideways such that ratcheting part 190 rotates about central axis 70. Optionally, ratcheting part 190 can include a pawl that engages teeth on a fixed ratchet member and prevents ratcheting part 190 from rotating backwards.

Ratcheting part 190 includes gear teeth 200 (FIGS. 29A and 29B) which are located closer to central axis 70 than angled teeth 196. First intermediate gear 192 includes outer gear teeth 202 that engage gear teeth 200, such that rotation of ratcheting part 190 causes intermediate gear 192 to rotate about axis 204 which is parallel to and offset from central axis 70. First intermediate gear 192 includes inner gear teeth 203. Second intermediate gear 193 includes gear teeth 205 that engaged inner gear teeth 203, such that rotation of first intermediate gear 192 causes second intermediate gear 193 to rotate. Dose counter part 194 includes gear teeth 206 that engage gear teeth 205, such that rotation of second intermediate gear 193 causes dose counter part 194 to rotate about central axis 70.

In FIGS. 28A and 29A, dose counter part 194 is a hollow cylinder with central passageway 220 in which container 12 is located. The dose counter part can be configured in other ways, as described below.

In FIGS. 30A-30C, device 10 has lock 50 that includes three rotatable parts: ratcheting part 190, intermediate gear 192, and dose counter part 194. Ratcheting part 190 is contacted and rotated by spreader 14. Intermediate gear 192 is contacted and rotated by ratcheting part 190. Dose counter part 194 is contacted and rotated by intermediate gear 192.

Spreader 14 includes a plurality of angled spreader teeth 195. When angled teeth 195 move into lock 50, lock 50 advances one step toward its locked state. Lock 50 is configured to advance by a total number of steps that corresponds to the total number of drug doses which device 10 is designed to deliver. The total number of steps establishes the numerical limit, previously described above, at which pump 16 can no longer be actuated by spreader 14.

Ratcheting part 190 includes angled teeth 196 and is constrained from moving axially relative to case 40. When spreader 14 is pushed down by the user to actuate pump 16, angled spreader teeth 195 engage angled teeth 196 of ratcheting part 190 and pushes teeth 196 sideways such that ratcheting part 190 rotates about central axis 70. Optionally, ratcheting part 190 may include a pawl that engages teeth on a fixed ratchet member and prevents ratcheting part 190 from rotating backwards.

Ratcheting part 190 includes gear teeth 200 (FIGS. 30A and 30B) which are located closer to central axis 70 than angled teeth 196. Intermediate gear 192 includes outer gear teeth 202 that engage gear teeth 200, such that rotation of ratcheting part 190 causes intermediate gear 192 to rotate about axis 204 which is parallel to and offset from central axis 70. Intermediate gear 192 includes inner gear teeth 203. Dose counter part 194 includes gear teeth 206 that engage gear teeth 203, such that rotation of intermediate gear 192 causes dose counter part 194 to rotate about axis 207 that is parallel to and offset from central axis 70 and axis 204.

Portion 208 of dose counter part 194 is visible through aperture 44 in case 40. Portion 208 is cylindrical. In FIG. 30C, portion 208 is illustrated schematically in a flattened state. Visual indicator 46 is disposed on portion 208. As dose counter part 194 rotates, visual indicator 46 shifts position so that a different area of visual indicator 46 becomes visible in aperture 44. Visual indicator 46 can be as previously described above.

In FIG. 30C, visual indicator 46 includes a graphical pattern, which may include changes in color, to indicate whether lock 50 is at or near the numerical limit, previously described above, at which pump 16 can no longer be actuated by spreader 14.

Figures 31A, 31B:
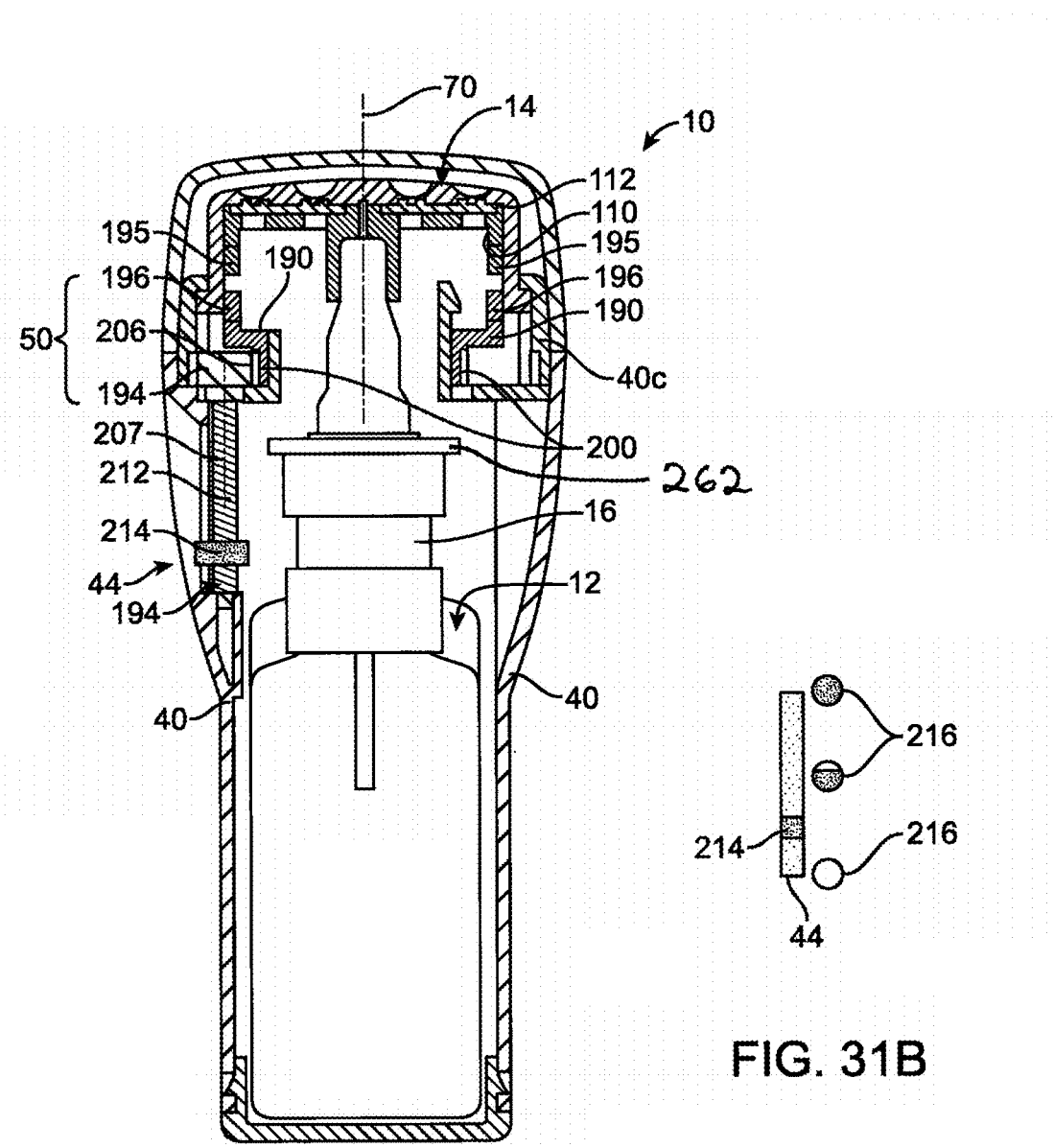
FIG. 31A is a section view showing an exemplary device for dispensing a drug.
FIG. 31B is a schematic view showing a portion of a movable indicator member which would be visible through an aperture of the device of FIG. 31A.

In FIGS. 31A and 31B, device 10 has lock 50 that includes ratcheting part 190 and dose counter part 194. Ratcheting part 190 is operatively coupled, in a direct manner, to dose counter part 194 without an intermediate gear. Ratcheting part 190 is contacted and rotated by spreader 14. Dose counter part 194 is contacted and rotated by ratcheting part 190.

Spreader 14 includes a plurality of angled spreader teeth 195. When angled teeth 195 move into lock 50, lock 50 advances one step toward its locked state. Lock 50 is configured to advance by a total number of steps that corresponds to the total number of drug doses which device 10 is designed to deliver. The total number of steps establishes the numerical limit, previously described above, at which pump 16 can no longer be actuated by spreader 14.

Ratcheting part 190 includes angled teeth 196 and is constrained from moving axially relative to case 40. When spreader 14 is pushed down by the user to actuate pump 16, angled spreader teeth 195 engage angled teeth 196 of ratcheting part 190 and pushes teeth 196 sideways such that ratcheting part 190 rotates about central axis 70. Optionally, ratcheting part 190 may include a pawl that engages teeth on a fixed ratchet member and prevents ratcheting part 190 from rotating backwards.

Ratcheting part 190 includes gear teeth 200 that are located closer to central axis 70 than angled teeth 196. Dose counter part 194 includes gear teeth 206 that engage gear teeth 200, such that rotation of ratcheting part 190 causes dose counter part 194 to rotate about axis 207 that is offset from and parallel to central axis 70.

Dose counter part 194 includes helical thread 212 and movable indicator member 214 that engages helical thread 212. Movable indicator part 214 functions as a visual indicator. Movable indicator member 214 is constrained from rotating around axis 207 but is not constrained from moving axially on dose counter part 194. When the user actuates pump 16 by pushing spreader 14 downward, dose counter part 194 rotates which causes movable indicator part 214 to move axially on helical thread 212. Movable indicator part 214 is visible through aperture 44 in case 40.

As shown in FIG. 31B, the position of movable indicator part 214 within aperture 44 can indicate whether lock 50 is at or near the numerical limit, previously described above, at which pump 16 can no longer be actuated by spreader 14. Graphic symbols 216 or characters can be disposed on case 40 to explain to the user the meaning of the position of movable indicator part 214.

In FIG. 32A-32G, device 10 has lock 50 that includes three rotatable parts: ratcheting part 190, intermediate gear 192, and dose counter part 194. Ratcheting part 190 is contacted and rotated by spreader 14. Intermediate gear 192 is contacted and rotated by ratcheting part 190. Dose counter part 194 is contacted and rotated by intermediate gear 192.

First portion 110 of spreader 14 includes a plurality of angled spreader teeth 195. When angled teeth 195 move into lock 50, lock 50 advances one step toward its locked state. Lock 50 is configured to advance by a total number of steps that corresponds to the total number of drug doses which device 10 is designed to deliver. The total number of steps establishes the numerical limit, previously described above, at which pump 16 can no longer be actuated by spreader 14.

Figure 32A:
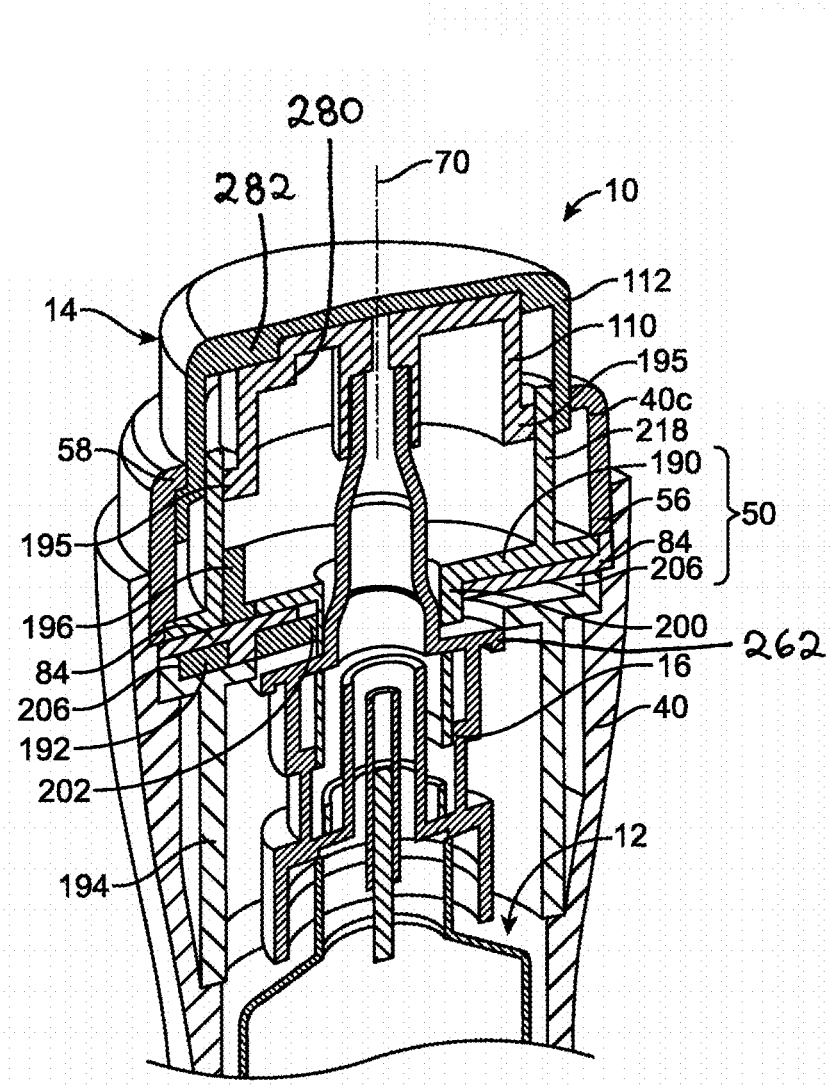
FIG. 32A is a perspective section view showing rotatable parts of a lock in an exemplary device for dispensing a drug.
Figure 32B:
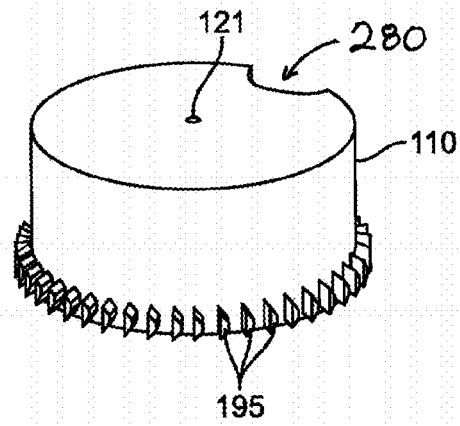
FIGS. 32B and 32C are perspective views showing exemplary components of a spreader in the device of FIG. 32A.
Figure 32C:
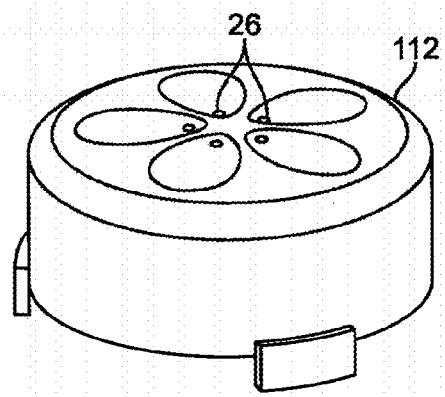
Figure 32D:
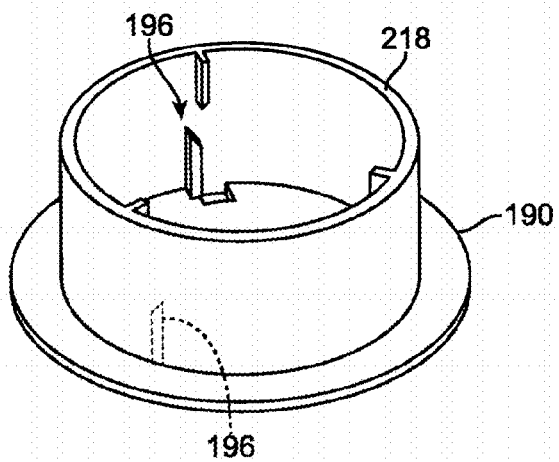
FIGS. 32D and 32E are perspective views showing an exemplary ratcheting part of a lock in the device of FIG. 32A.
Figure 32E:
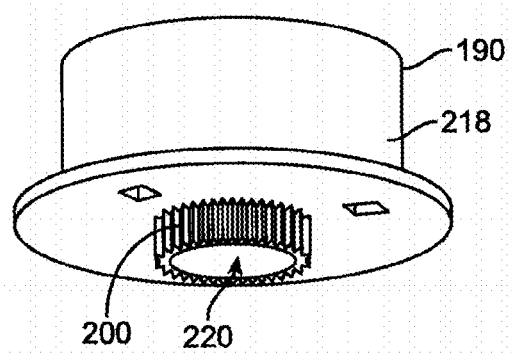

As shown in FIGS. 32A and 32D, ratcheting part 190 includes angled teeth 196 and is constrained from moving axially relative to case 40. When spreader 14 is pushed down by the user to actuate pump 16, angled spreader teeth 195 engage angled teeth 196 of ratcheting part 190 and pushes teeth 196 sideways such that ratcheting part 190 rotates about central axis 70. Optionally, ratcheting part 190 can include a pawl that engages teeth on fixed ratchet member 84 and prevents ratcheting part 190 from rotating backwards.

Ratcheting part 190 includes gear teeth 200 (FIGS. 32A and 32E) which are located closer to central axis 70 than angled teeth 196. Intermediate gear 192 includes gear teeth 202 that engage gear teeth 200, such that rotation of ratcheting part 190 causes intermediate gear 192 to rotate about an axis that is parallel to and offset from central axis 70. Dose counter part 194 includes gear teeth 206 that engage gear teeth 202, such that rotation of intermediate gear 192 causes dose counter part 194 to rotate about central axis 70. Dose counter part 194 includes a portion that is visible through aperture 44 (FIG. 32F) in case 40 in the same manner described for device 10 of FIG. 27A.

Ratcheting part 190 includes cylindrical guide wall 218. Angled teeth 196 are attached to cylindrical guide wall 218. Cylindrical guide wall 218 is disposed between first portion 110 and second portion 112 of spreader 14. Spreader angled teeth 195 slide against cylindrical guide wall 218 when spreader 14 is pushed down by the user to actuate pump 16. Ratcheting part 190 has central through hole 220 through which a top portion of container 12 extends.

Referring to FIG. 32G, spreader 14 moves up and down, within the central opening of case top 40C, in a direction parallel to central axis 70. Spreader 14 moves relative to case top 40C and case 40. Case top 40C can be permanently secured to case 40. Ratcheting part 190 does not travel up and down relative to case top 40C and case 40. Ratcheting part 190 rotates about central axis 70 relative to case top 40C and case 40. Ratcheting part 190 rotates by one increment with each downward movement of spreader 14 into case top 40C.

Case top 40C keeps various components in place. Bottom edge 56 of case top 40C engages flange portion 222 of ratcheting part 190, which prevents ratcheting part 190 from moving up away from case 40. Inner lip 58 of case top 40C engages protruding portion 60 of spreader 14 so as to prevent spreader 14 from separating away from pump 16.

Ring 84 is disposed between flange portion 222 of ratcheting part 190 and dose counter part 194. Ring 84 holds intermediate gear 192 at the position shown such that the gear teeth of intermediate gear 192 mate with the gear teeth of ratcheting part 190 and dose counter part 194.

FIG. 32G shows the gear teeth of intermediate gear 192 engaged with gear teeth 206 of ratcheting part 190. The lock (generally indicated by numeral 50 in FIG. 32A) includes ratcheting part 190, intermediate gear 192, and dose counter part 194. Dose counter part 194 includes lock member 78 which moves incrementally (together with dose counter part 194) with each rotation step taken by lock 50. In FIG. 32G, lock member 78 is in the form of a filled area between two teeth 206 of dose counter part 194.

Lock member 78 moves closer to its lockout position with each step of lock 50 that results from downward movement of spreader 14 and from actuation of pump 16. When not at the lockout position, lock member 78 is not engaged with intermediate gear 192, so dose counter part 194 (together with lock member 78) is capable of rotating when spreader 14 is pushed downward by the user. When at the lockout position (as shown in FIG. 32G), lock member 78 is engaged with intermediate gear 192. Thereafter, when the user of device 10 attempts to actuate pump 16 again, lock member 78 obstructs any further movement. Lock member 78 prevents further rotation of intermediate gear 194, which prevents further rotation of ratcheting part 190, which prevents downward movement of spreader 14, and which prevents pump 16 from being actuated. Dose counter part 194 can be designed such that the location of lock member 78 will determine the numerical limit of lock 50, which corresponds to the number of times pump 16 can be actuated. The numerical limit of lock 50 is reached with lock member 78 obstructs intermediate gear 192 as shown in FIG. 32G.

In FIG. 32B, spreader 14 includes a single set of angled spreader teeth 195. Optionally as shown, spreader teeth 195 are formed on and circumferentially arranged around the outer surface of spreader first portion 110. When device 10 is assembled, spreader teeth 195 are disposed within the second portion 112 of spreader 114. As shown in FIG. 32A, cylindrical guide wall 218 of ratcheting part 190 is disposed between spreader teeth 195 and second portion 112. This arrangement allows spreader teeth 195 to contact and rotatably push angled teeth 196 of ratcheting part 190.

The components of the lock may be retained in position by various means. An exemplary means for retaining such components is shown in FIGS. 33A and 33B.

In FIGS. 33A and 33B, device 10 has lock 50 that includes three rotatable parts: ratcheting part 190, intermediate gear 192, and dose counter part 194. These three parts operate in the same way as described in FIGS. 32A-32G, except as described below.

It is to be understood that dose counter part 194 in FIGS. 33A-B includes lock member 78 as in FIG. 32G. Lock member 78 is directly attached to or is integrally formed on dose counter part 194. The lock member 78 has a plurality of positions including a lockout position. Plurality of positions defines a circular travel path of the lock member. Each change in position of the lock member is an incremental step on the circular travel path around the container. The lock moves the lock member from one of the positions to the next position when the spreader actuates the pump. The lock member reaches the lockout position when the pump has been actuated to the numerical limit of the lock. When at the lockout position, the lock member obstructs a tooth of intermediate gear 192, which prevents movement of the spreader relative to the case and prevents the spreader from actuating the pump.

Differences between lock components in FIGS. 32A-32G versus FIGS. 33A-B are described below.

Retaining ring 84 shown in FIG. 32F is replaced by upper retaining ring 250 and lower retaining ring 252 in FIGS. 33A-B. When device 10 is fully assembled, upper retaining ring 250 and lower retaining ring 252 are fixed to each other and to device case 40. Upper retaining ring 250 and lower retaining ring 252 do not move relative to each other, and they do not move relative to case 40. Upper retaining ring 250 and lower retaining ring 252 are fixed to each other by way of one or more cantilevered clips 254, ultrasonic welding, screws, or other means. As described below, upper retaining ring 250 and lower retaining ring 252 keep the ratcheting part 190, intermediate gear 192, and dose counter part 194 properly engaged with each other.

Lower retaining ring 252 includes support ledge 256, spindle 258, and click feature 260. Support ledge 256 supports dose counter part 194 without interfering with gear teeth 206 of dose counter part 194. Dose counter part 194 rotatably slides on support ledge 256 with each actuation of the pump and advancement of the lock previously described. Dose counter part 194 rotates about central axis 70.

Spindle 258 supports intermediate gear 192. Intermediate gear 192 rotatably slides on and around spindle 258 with each actuation of the pump and advancement of the lock previously described. Spindle 258 is positioned so that intermediate gear 102 engage gear teeth 206 of dose counter part 194. Spindle 258 constrains rotation of intermediate gear 192 about axis 204 which is offset from central axis 70.

Click feature 260 is in the form of a flexible cantilevered arm that extends radially inward toward central axis 70. Click feature 260 has a radial length that allows for mechanical interference with a projection of the device pump. For example, the projection may be flange 262 of pump 16 shown in FIGS. 1, 28A, 29A, 30A, 31A, and 32A. Pump 16 may have another type of projection for interacting with click feature 260. Before the user presses device spreader 14, the pump projection is at is normal position above click feature 260. When the user starts to press spreader 14, the pump projection pushes down on the tip of click feature 260.

With increased pressure applied to spreader 14, the tip deflects and eventually flicks or snaps to a position above the pump projection, which produces an audible click sound. The pump projection is now located below click feature 260. Next, when the user releases spreader 14, a spring or other biasing device inside pump 16 returns the pump projection to its normal position. When moving to its normal position, the pump projection deflects the tip of click feature 260 upward, which causes the tip to snap to a position below the pump projection and thereby produce another audible click.

Upper retaining ring 250 includes fingers 264 that retain flange portion 222 of ratcheting part 190. Fingers 264 retain ratcheting part 190 so that gear teeth 200 of ratcheting part 190 remain engaged with intermediate gear 192. Upper retaining ring 250 includes angled teeth 196A and 196B. Tooth 196A and tooth 196B form a pair, and upper retaining ring 250 may have two, three, or more pairs of teeth 196A and 196B. Angled teeth 196A and 196B are circumferentially arranged around central axis 70. Gear teeth 200 are also circumferentially arranged around central axis 70 but are located closer to central axis 70 than angled teeth 196A and 196B. Gear teeth 200 operate in the same way as gear teeth 200 described in FIGS. 28A, 29A, 30A, 31A, and 32A.

Teeth 196A are upward facing in that their sloped surfaces 197 face upward. Teeth 196B are downward facing in that their sloped surfaces 197 face downward. Before the user presses spreader 14, teeth 196B are already disposed between pairs of spreader teeth 195 (FIG. 32B). When the user presses spreader 14 downward, teeth 196B help to guide spreader teeth 195 into contact with sloped surfaces 197 of upward facing teeth 196A. When contact occurs, spreader teeth 195 cause ratcheting part 190 to rotate as previously described for previous figures of the present specification. Tips of the sloped surfaces 197 are axially spaced apart by axial gap 199. Axial gap 199 is sized to permit passage of spreader teeth 195 during rotation of ratcheting part 190. Due to rotation of ratcheting part 190, spreader teeth 195 become axially aligned with sloped surfaces 197 of downward facing teeth 196B. When the user releases spreader 14, spreader teeth 195 move up and return to their original position. Each tooth 196B is now disposed between a different pair of spreader teeth 195. Tooth 196B prevents rotation of ratcheting part 190 until the user presses spreader 14 again.

When a spreader tooth 195 passes through axial gap 199 and then moves up to its original position, spreader tooth 195 contacts sloped surface 197 of downward facing tooth 196B. When contact occurs, spreader tooth 195 causes ratcheting part 190 to rotate further in the same direction. Rotation with both downward and upward motion of spreader tooth 195 (and spreader 14) allows for a greater amount of rotation of ratcheting part 190 which each drug dose delivered. Due to action of intermediate gear 192, greater rotation of ratcheting part 190 translates to even greater rotation of dose counter part 194 so that a change in position of printed numerical or graphic indicators on dose counter part 194 can be more easily perceived by the user.

The lock components described in FIGS. 33A and 33B cooperate with spreader first portion 110 and second portion 112 in the same way as the lock components described in FIGS. 32A-32G.

FIGS. 33A and 33B illustrate a design for spreader 14 that can be combined with any of the designs for lock 50 described above.

Spreader first portion 110 and second portion 112 are both made of rigid material. Proper operation of spreader 14 does not require any of first portion 110 and second portion 112 to flex or bend in relation to the other. Also, there is no flexible valve member for sealing drug passageway 24 between first portion 110 and second portion 112. Drug passageway 24 does not move from a collapsed state to an open state. Drug passageway 24 remains open at all times.

Figure 34A:
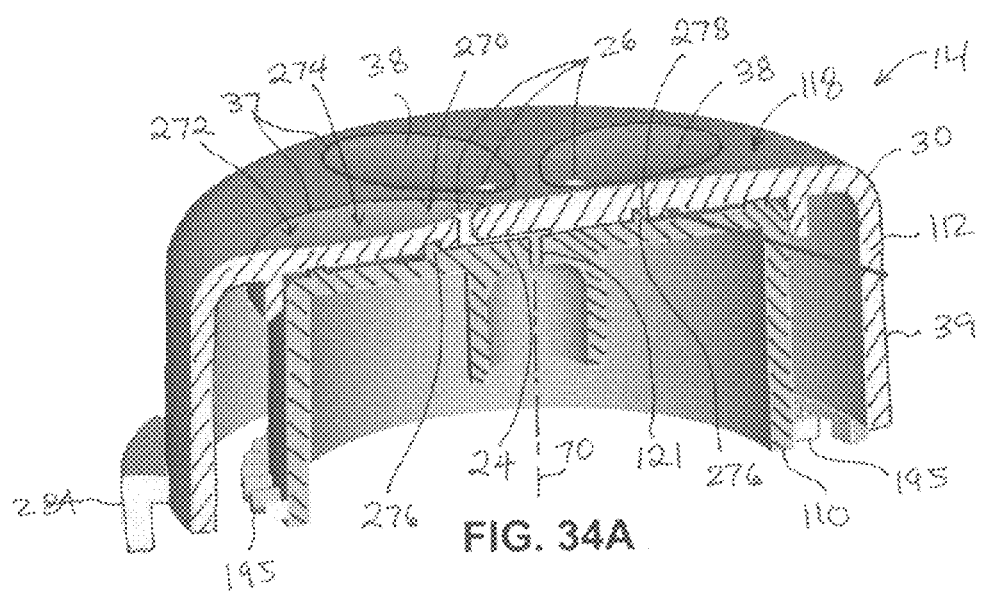
FIG. 34A is a perspective section view through a first cut plane of an exemplary spreader for any drug dispensing device herein.

Upper surface 118 of second portion 112 is the same as what is shown in FIGS. 20 and 32C. In FIGS. 20, 32C, and 34A, drug channels 38 are a petal-shaped ovals. The oval is defined by channel perimeter 37. Each oval perimeter 37 has round narrow end 270 and round wide end 272. Round wide end 272 has a radius of curvature greater than that of round narrow end 270. Round narrow ends 270 converge toward each other. Drug channels 38 are arranged radially with round narrow ends 270 located closer to central axis 70 of spreader 14 as compared to round wide ends 272. That is, the radial distance from central axis 70 to round narrow ends 270 is less than the radial distance from central axis 70 to round wide ends 272. Round wide ends 272 are located closer to peripheral edge 30 of spreader 14 as compared to narrow ends 270. That is, the radial distance from peripheral edge 30 to round wide ends 272 is less than the radial distance from peripheral edge 30 to round narrow ends 270. All drug outlets 26 are located closer to first portion aperture 121 than peripheral edge 30. This allows the drug to be more quickly delivered to the surface than if drug outlets 26 were located further away from first portion aperture 121.

As shown in FIG. 34A, each drug channel 38 is a concave depression having a depth that varies according to distance from central axis 70. The depth is shallower at round narrow end 270 and round wide end 272 than at groove central region 274. Round narrow end 270, groove central region 274, round wide end 272, are also referred to as a first groove region, second groove region, and third groove region, respectively. The depth is greatest at groove central region 274 (second groove region). There is no drug outlet present at groove central region 274. Drug outlet 26 is located at round narrow end 270 (first groove region). When the drug exits drug outlet 26, it can be immediately spread on the user's skin. Since drug outlet 26 is not located at the deepest region of drug channel 38, the drug is less likely to collect or pool within drug channel 38 without making contact with the skin. Excess amounts of the drug, if any, may tend to move radially outward from outlet 26 toward peripheral edge 30. When moving radially outward, the excess amounts of the drug may then be captured by groove central region 274 due to the greater groove depth at groove central region 274. This can inhibit the drug from being pushed out beyond peripheral edge 30 where it can drip down sides 39 of spreader 14. As the user rubs spreader 14 on the skin, the excess drug collected within groove central region 274 can be pushed toward peripheral edge 30 and into round wide end 272 of the drug channel. As previously mentioned, drug channel 38 becomes shallower at round wide end 272. At the same time, drug channel 38 becomes wider at round wide end 27, so the excess drug can be distributed over a greater surface area of the spreader 14 before it reaches peripheral edge 30. By spreading the drug over a greater surface area, the drug is more likely to be transferred onto the user's skin rather than dripping down sides 39 of the spreader.

There five petal-shaped oval drug channels 38 on second portion upper surface 118. There is a single drug outlet 26 in each drug channel 38. In other aspects, there can be a lesser or greater number of petal-shaped oval drug channels 38. Also, there can be two or more drug outlets in each drug channel 38. The number of drug channels and outlets may depend on the viscosity of the drug composition, the surface area size of the spreader, and/or other factors.

The concept of placing the drug outlets at a shallow region (e.g., round narrow end or first groove region) of the drug channel, instead of the deepest region of the channel (e.g., central groove region or second groove region), may also be applied to any of the concentric annular drug channels described above, such as in FIGS. 3, 4, 8 and others.

Figure 34B:
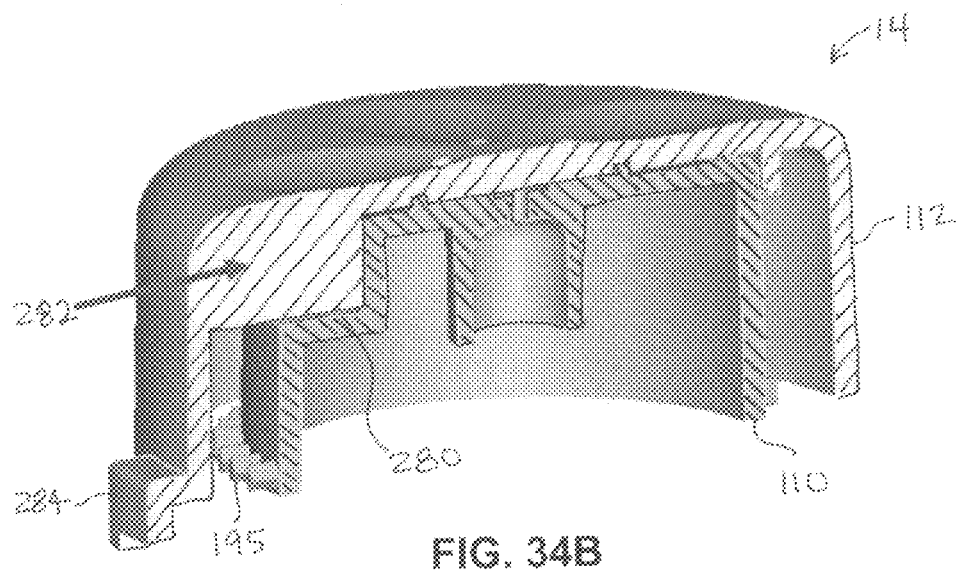
FIG. 34B is a perspective section view through a second cut plane of the spreader of FIG. 34A.
Figure 35:
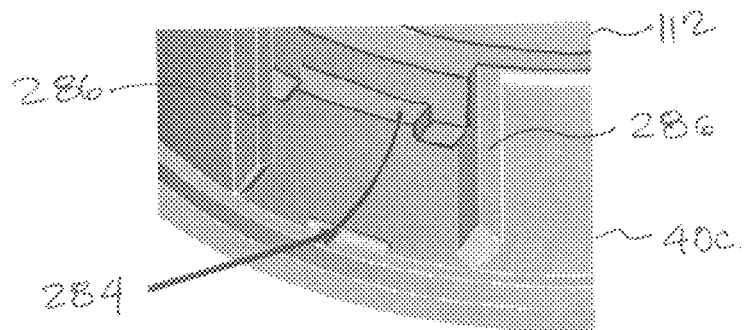
FIG. 35 is a perspective view of a portion of drug dispensing device case, showing exemplary ribs for retaining the spreader of FIGS. 34A and 34B.

Referring again to FIGS. 34A and 34B, first portion aperture 121 receives the drug and distributes it to drug outlets 26 via straight delivery grooves formed into the upper surface of spreader first portion 110 or on the lower surface of spreader second portion 112. Delivery grooves can be the same as grooves 124 in FIG. 25A. There is a single groove for each drug outlet 26. Delivery grooves are encircled by annular rib 276 formed on the upper surface of first portion 110. Annular rib 276 is received within annular groove 278 formed into the lower surface of second portion 112. Annular rib 276 and annular groove 278 prevent or inhibit the drug from traveling beyond drug outlets 26 so that a maximum amount of the drug can reach the outer surface 118 of the spreader in the shortest amount of time. Portions of the first portion upper surface and the second portion lower surface can be fused together, such as by ultrasonically welding or other means, to help bring a maximum amount of the drug to the outer surface quickly. For example, areas between delivery grooves can be ultrasonically fused together so that the drug is encouraged to travel only in the delivery grooves. Additionally or alternatively, annular rib 276 and annular groove 278 may be ultrasonically welded together to encourage the drug to exit from outlets 26.

As shown in FIG. 34B, spreader first portion 110 has alignment feature 280 which may facilitate assembly and proper alignment of first portion 110 with second portion 112, components of lock 50 and/or other components of device 10.

Alignment feature 280 may prevent rotation of first portion 110 when the user presses spreader 14. As described above, when the user pushes spreader 14 down, spreader teeth 195 of first portion 110 contacts the teeth of ratcheting part 190, which causes ratcheting part 190 to rotate forward. When contact occurs, it is desirable to prevent first portion 110 from rotating backward so that a maximum amount of torque is applied to ratcheting part 190. In FIG. 34B, alignment feature 280 is in the form of depression formed into the second portion upper surface. Depression 280 receives protrusion 282 formed on the second portion lower surface. Depression 280 and protrusion 282 can be as shown in FIGS. 32A and 32B.

Engagement between depression 280 and protrusion 282 ensures that spreader first portion 110 does not rotate relative to second portion 112. Spreader second portion 112 includes arm 284 which extends radially outward and engages vertical ribs 286 in case top 40C, as shown in FIG. 35. Ribs 286 run parallel to central axis 70 (FIG. 34A). FIG. 35 shows a view looking up from beneath arm 284 when arm 284 is seated between a pair of ribs 286 of case top 40C. An exemplary case top 40C is shown in FIG. 8. Ribs 286 allow arm 284 to move linearly when the user presses spreader 14. Arm 284 slides between ribs 286 but is prevented from rotating relative to case top 40C. Spreader second portion 112 may have two, three, or more arms 284. On case top 40C, there would be one pair of ribs 286 for each arm 284.

Although the descriptions above sometimes refer to topical administration of a drug to the user's axilla (armpit), it will be appreciated that device 10 (or spreader 14 or container 12 in combination with other types of devices) can be used to administer a drug (e.g., glycopyrronium tosylate or others) to the user's hand, feet, forehead, and/or other parts of the anatomy as indicated above.

Although the descriptions above refer to dispensing glycopyrronium tosylate, which can be used to treat hyperhidrosis, it will be appreciated that device 10 can be used to treat other medical conditions, diseases, or ailments. Device 10 (or spreader 14 or container 12 in combination with other types of devices) can be used for administration of many types of compositions and drugs as indicated above.

While several particular forms of the invention have been illustrated and described, it will also be apparent that various modifications can be made without departing from the scope of the invention. It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

What is claimed is:

1. A device for dispensing a drug, the device comprising:
- a case;
- a spreader for spreading a drug on the skin, the spreader extending out of the case;
- a container for the drug, the container disposed within the case and including a pump configured to be actuated to deliver the drug to the spreader; and
- a lock within the case, the lock configured to prevent actuation of the pump when the pump has been actuated to a numerical limit of the lock,
- wherein the lock includes a dose counter part coupled to the spreader, the dose counter part includes a visual indicator that is visible through an aperture in the case, the dose counter part rotates with axial movement of the spreader into the case, and the rotation of the dose counter part moves the visual indicator within the aperture, and
- wherein the lock includes a ratcheting part operatively coupled to the dose counter part, the ratcheting part rotates with axial movement of the spreader into the case, the rotation of the ratcheting part rotates the dose counter part, and the ratcheting part is operatively coupled to the dose counter part by one or more intermediate gears.

2. The device of claim 1, wherein the spreader includes a plurality of spreader teeth, the spreader teeth rotate the ratcheting part with axial movement of the spreader into the case.

3. The device of claim 2, wherein the spreader includes a first portion and a second portion, the first portion is mounted on a tip of the container, the second portion covers the first portion and forms an exposed surface of the spreader outside of the case, the ratcheting part includes a cylindrical wall disposed between the first portion and the second portion, the ratcheting part includes a plurality of angled teeth on the cylindrical wall, and the angled teeth are configured to engage the spreader teeth.

4. The device of claim 3, wherein the ratcheting part includes gear teeth operatively coupled to the dose counter part, the gear teeth are closer to a rotation axis of the ratcheting part than the angled teeth of the ratcheting part.

5. The device of claim 1, wherein the ratcheting part includes a through hole in which the container extends.

6. The device of claim 1, wherein the axial movement of the spreader into the case is in a direction parallel to a central axis of the spreader.

7. The device of claim 6, wherein a rotation axis of the dose counter part is coincident with the central axis of the spreader.

8. The device of claim 1, wherein the drug is: tretinoin; benzocaine, butamben, dibucaine, lidocaine, oxybuprocaine, pramoxine, proparacaine, proxymetacaine, or tetracaine; erythromycin, benzoyl peroxide, clindamycin, penederm, sodium sulfacetamide, adapalene or Tazorac; becaplermin; minoxidil; tigecycline, clindamycin or butenafine; podofilox; betamethasone; luliconazole, terbinafine or terbinafine hydrochloride; tacrolimus; azelaic acid; ivermectin; ingenol mebutate; polidocanol; mechlorethamine; efinaconazole; glycopyrronium bromide; glycopyrronium tosylate; or an aluminum salt.

9. The device of claim 1, wherein the drug is for administration to any region of the skin.

10. The device of claim 1, wherein the drug is for administration to: one or more axilla; one or more hands; one or more palms; one or more feet; one or more foot soles; the face; the forehead; the back; the lower back; the upper back; or to the genitals.

11. A device for dispensing a drug, the device comprising:
a container for a drug; and
a spreader connected to the container and having an exposed surface for spreading the drug on skin, the exposed surface including a plurality of drug outlets that dispense the drug from the container, the exposed surface further including a plurality of concave drug channels arranged around a central axis of the spreader, at least some of the drug outlets being located within the drug channels,
each drug channel having an oval perimeter, the oval perimeter defined by a round narrow end, a round wide end, and a groove central region between the round narrow end and the round wide end, the round wide end having a radius of curvature greater than that of the round narrow end, the round narrow ends of the oval perimeters converge toward each other and are closer to the central axis than the round wide ends,
each drug channel having a depth that varies within the oval perimeter, the depth being greater at the groove central region than at the round narrow end and the round wide end.

12. The device of claim 11, wherein at least some of the drug outlets are located in the round narrow end of the oval perimeter of each drug channel.

13. The device of claim 11, wherein none of the drug outlets present on the spreader are located in any of the round wide ends of the oval perimeters of the drug channels.

14. The device of claim 11, wherein none of the drug outlets present on the spreader are located in any of the groove central regions of the oval perimeters of the drug channels.

15. The device of claim 11, wherein all of the drug outlets present on the spreader are located within the oval perimeters of the drug channels.

16. The device of claim 11, wherein spreader includes:
a first portion having a first portion upper surface and a first portion lower surface, the first portion lower surface coupled to the container; and
a second portion disposed over the first portion and having a second portion upper surface and a second portion lower surface facing the first portion upper surface, the second portion upper surface being the exposed surface in which the drug channels and drug outlets are formed, and
wherein the first portion upper surface and the second portion lower surface define drug passageways that extend to the drug outlets, and areas of the first portion upper surface between the drug passageways are in contact with the second portion lower surface.

17. A device for dispensing a drug, the device comprising:
a spreader for spreading the drug, the spreader including a first portion and a second portion, the first portion having a first portion upper surface and a first portion lower surface, the second portion having a second portion upper surface for applying the drug onto skin and a second portion lower surface, the second portion lower surface is disposed on and in contact with the first portion upper surface, wherein
a drug inlet is formed through the first portion lower surface,
a drug passageway extends from the drug inlet to an aperture formed in the first portion upper surface,
at least one concave drug channel is formed in the second portion upper surface, each drug channel has a depth that varies, each drug channel includes a first groove region and a second groove region, the depth is greatest at the second groove region as compared to all other regions of the drug channel,
a plurality of drug outlets are formed through the second portion upper surface, at least some of the drug outlets are located in the first groove region of the at least one concave drug channel, and none of the drug outlets present on the second portion upper surface are located in any second groove region on the second portion upper surface.

18. The device of claim 17, wherein all the drug outlets present on the second portion upper surface are located in the first groove region of the at least one concave drug channel.

19. The device of claim 17, wherein the at least one concave drug channel includes two or more concave drug channels, each of the drug channels includes its own first groove region and second groove region, the depth of the drug channel is greatest at the second groove region as compared to all other regions of the drug channel.

20. The device of claim 17, wherein each concave drug channel has an oval perimeter, the oval perimeter is defined by the first groove region, the second groove region, and a third groove region, the second groove region is disposed between the first groove region and the third groove region, the third groove region has a radius of curvature at the perimeter that is greater than that of the first groove region, the first groove regions of the oval perimeters converge toward each other and are closer to a central axis of the spreader than the third groove region, and the depth is greater at the second groove region than at the first and third groove regions.

21. The device of claim 17, wherein the aperture formed in the first portion upper surface provides the drug to all the drug outlets, and none of the drug outlets are located directly above the aperture.

22. The device of claim 17, wherein device further comprises a container for the drug, the container coupled to the drug inlet formed through the first portion lower surface, wherein the first portion upper surface and the second portion lower surface define drug passageways that extend from the aperture formed in the first portion upper surface to the drug outlets.

* * * * *